United States Patent [19]

Trybulski et al.

[11] Patent Number: 5,451,685
[45] Date of Patent: Sep. 19, 1995

[54] SUBSTITUTED OXOTREMORINE DERIVATIVES

[75] Inventors: Eugene J. Trybulski, Park Ridge, N.J.; Richard H. Kramss, Newburgh; Herbert Brabander, Nanuet, both of N.Y.

[73] Assignee: American Cyanamid Company, Wayne, N.J.

[21] Appl. No.: 274,604

[22] Filed: Jul. 13, 1994

Related U.S. Application Data

[62] Division of Ser. No. 690,749, Apr. 24, 1991, Pat. No. 5,356,885.

[51] Int. Cl.⁶ .............. C07D 401/06; C07D 403/06; C07D 207/27
[52] U.S. Cl. .................... 548/550; 548/406; 548/524; 546/208
[58] Field of Search ............ 548/550, 406, 524; 546/208

[56] References Cited

U.S. PATENT DOCUMENTS 3,920,824 11/1975 Rajadhyaksha .............. 514/274
4,065,471 12/1977 Dickinson .............. 260/326.5 X
4,833,139 5/1989 Martin .............. 514/327.8
4,937,235 6/1990 Trybulski .............. 514/63

*Primary Examiner*—David B. Springer
*Attorney, Agent, or Firm*—Richard K. Jackson

[57] ABSTRACT

This disclosure describes novel substituted oxotremorine derivatives of formula I having nitrogen, oxygen or sulfur groups and the prodrug forms of these derivatives. The compounds have cholinergic activity. Also disclosed are methods for treating diseases of the central nervous system in mammals employing the compounds, pharmaceutical preparations containing the compounds and the processes for the production of the compounds.

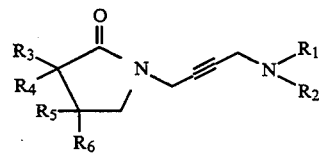

FORMULA I

1 Claim, No Drawings

SUBSTITUTED OXOTREMORINE DERIVATIVES

CROSS REFERENCE TO RELATED APPLICATIONS

This is a divisional of application Ser. No. 07/690,749 filed on Apr. 24, 1991 now U.S. Pat. No. 5,356,885.

This application is related to applicant's application Ser. No. 570,950, now U.S. Pat. No. 5,089,518, which is a division of Ser. No. 481,924, now U.S. Pat. No. 4,952,600 which is a division of Ser. No. 300,447, now U.S. Pat. No. 4,937,235.

BACKGROUND OF INVENTION

The invention relates to compounds, pharmaceutical compositions and to the use of the compounds for the manufacture of pharmaceuticals.

A chronic deficiency in central cholinergic function has been implicated in a variety of neurologic and psychiatric disorders, including senile dementia of the Alzheimer's type (SDAT), tardive dyskinesia, Pick's disease and Huntington's chorea. Postmortem neurochemical investigations of patients with SDAT have demonstrated a reduction in presynaptic markers for acetylcholine utilizing neurons in the hippocampus and the cerebral cortex [P. Davies and A. J. R. Maloney, Lancet, 1976, 1403, (1976); E. K. Perry, R. H. Perry, G. Blessed, B. E. Tomlinson, J. Neurol.Sci., 34, 247, (1976)]. The basis for the cholinergic abnormality is unclear, but evidence suggests that the cholingergic neurons in the nucleus basalis of Meynert may selectively degenerate in SDAT [J. T. Coyle, D. J. Price, M. R. DeLong, Science, 219, 1184, (1983)]. If this degeneration plays a role in behavior symptoms of the disease, then a possible treatment strategy would be to compensate for the loss of cholinergic output to the cortex and hippocampus.

In an aged monkey animal model, designed to mimic the symptoms of SDAT, the direct muscarinic agonists arecoline [R. T. Bartus, R. L. Dean, B. Beer, Neurobiology of Aging, 1, 145, (1980)] and oxotremorine [R. T. Bartus, R. L. Dean, B. Beer, Psychopharmacology Bulletin, 19, 168, (1983)] produced significant improvement in performance. These results in aged monkeys were corroborated in SDAT patients with arecoline which produced a more consistent improvement when compared to the anticholinergic inhibitor physostigmine [J. E. Christie, A. Shering, J. Ferguson, A. M. Glen, British Journal of Psychiatry, 138, 46, (1981)].

These animal behavioral and clinical results have instigated significant efforts in a search for a muscarinic agonist which will selectively compensate for the loss of cholinergic input in the hippocampus and cerebral cortex. However, the search must be refined to seek agonists which will not affect significantly the remaining body cholinergic functions. The recent disclosure that muscarinic receptors are not all the same but exist as a heterogeneous population of receptors substantiates the possibility for the discovery of a selective muscarinic agonist [T. I. Bonner, N. J. Buckley, A. C. Young, M. R. Brann, Science, 237, 527, (1987)].

The methodical methylation of the muscarinic agonist oxotremorine and its derivatives has been studied in the search for a selective muscarinic agonist [B. Ringdahl, J. Med. Chem., 31, 683, (1988); B. Ringdahl, "Structural Determinants of Muscarinic Agonist Activity" The Muscarinic Receptors, J. H. Brown Ed., The Humana Press, Clifton, N.J., 1989, 151]. The methodical substitution of a methyl group onto oxotremorine can probe the steric non-polar environment of the muscarinic agonist for its neurotransmitter-receptor-complex.

The present invention describes the preparation of oxotremorine derivatives having polar substituted oxygen and substituted sulfur groups. This series of compounds goes beyond the initial study by Ringdall. In addition to exploring the steric environment of the muscarinic agonist for its neurotransmitter complex, the compounds of the present invention probe possible auxiliary polar interactions with one of the muscarinic receptors.

SUMMARY OF THE INVENTION

This invention is concerned with new compounds of formula I which have cholinergic activity; with methods of treating diseases of the central nervous system in mammals employing these new compounds; with pharmaceutical preparations containing these compounds; and with processes for the production of these compounds.

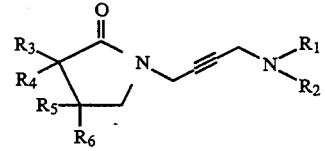

FORMULA I

In formula I, $R_1$ and $R_2$ are $(C_1-C_6)$alkyl or $R_1$ is $(C_1-C_6)$alkyl and $R_2$ is $-(CH_2)_n-R_{17}$ where $n=2-6$ and $R_{17}$ is selected from hydroxy, $(C_1-C_{10})$acyloxy, trialkylsilyloxy or $R_1$ and $R_2$ taken together with their associated N(itrogen) are selected from the group consisting of aziridine, azetidine, pyrrolidine, imidazole, piperidine or moieties of the formula:

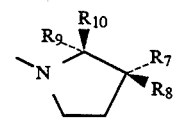

where $R_7$ and $R_8$ are independently selected from $(C_1-C_{10})$acyloxy, $(C_1-C_6)$alkoxy, aroyloxy, substituted aroyloxy, hydroxy, thio, $(C_1-C_6)$alkythio, $(C_1-C_6)$alkyldithio, $(C_1-C_6)$acylthio, trialkylsilyloxy or hydrogen; $R_9$ and $R_{10}$ are hydrogen, hydroxymethyl, trialkylsilyloxymethyl, or halomethyl, (wherein halo is chloro, bromo, or iodo) with the proviso that only one of $R_7, R_8, R_9$ and $R_{10}$ can be one of the above disclosed substituents other than hydrogen; $R_3$ and $R_4$ are independently selected from hydrogen, amino, azido, $(C_1-C_6)$alkyl, $(C_1-C_{10})$acyloxy, $(C_1-C_{10})$alkoxycarbonyl, $(C_1-C_{10})$alkylaminocarbonyloxy, $(C_1-C_{10})$dialkylaminocarbonyloxy, $(C_1-C_6)$alkoxy, aroyloxy, substituted aroyloxy, hydroxy, thio, $(C_1-C_6)$alkythio, $(C_1-C_6)$alkyldithio, or $(C_1-C_6)$acylthio with the proviso that one of $R_3$ or $R_4$ is hydrogen or $(C_1-C_6)$alkyl; $R_5$ and $R_6$ are independently selected from hydrogen, amino, azido, $(C_1-C_{10})$acyloxy, $(C_1-C_{10})$alkoxy-carbonyloxy, $(C_1-C_{10})$alkylaminocarbonyloxy, $(C_1-C_{10})$dialkylaminocarbonyloxy, $(C_1-C_6)$alkoxy, aroyloxy, $(C_1-C_6)$alkyldithio, substituted aroyloxy, hydroxy, thio, $(C_1-C_6)$alkylthio, $(C_1-C_6)$alkyldithio or $(C_1-C_{10})$a- cylthio with the proviso that when $R_3$ and $R_4$ are other than hydrogen, $R_5$ and $R_6$ are hydrogen.

DESCRIPTION OF THE INVENTION

The novel compounds of the present invention may be readily prepared in accordance with one or more of the following reaction schemes wherein $R_1'$ and $R_2'$ are $(C_1-C_6)$ alkyl, or $R_1'$ is $(C_1-C_6)$alkyl and $R_2'$ is —$(CH_2)_n$—$R_{17}$ where n=2-6 and $R_{17}$ is selected from hydroxy, $(C_1-C_{10})$acyloxy or trialkylsilyloxy or $R_1'$ and $R_2'$ taken together with their associated N(itrogen) are selected from the group consisting of pyrrolidine, piperidine or moieties of the formula:

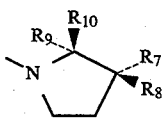

where $R_7$ and $R_8$ are independently selected from $(C_1-C_{10})$acyloxy, $(C_1-C_6)$alkoxy, aroyloxy, substituted aroyloxy, hydroxy, thio, $(C_1-C_6)$alkythio, $(C_1-C_6)$alkyldithio, $(C_1-C_6)$acylthio, trialkylsilyloxy or hydrogen; with the proviso that when one or both of $R_7$ and $R_8$ are hydrogen, $R_9$ and $R_{10}$ are hydrogen, hydroxymethyl or trialkylsilyloxymethyl with the proviso that only one of $R_7,R_8$, $R_9$ and $R_{10}$ can be one of the above disclosed substituents other than hydrogen; $R_3'$ and $R_4'$ are independently selected from hydrogen, $(C_1-C_6)$alkyl, hydroxy, $(C_1-C_{10})$acyloxy, $(C_1-C_{10})$alkoxycarbonyloxy, $(C_1-C_{10})$alkylaminocarbonyloxy $(C_1-C_{10})$dialkylaminocarbonyloxy, or $(C_1-C_6)$alkoxy with the proviso that only one of $R_3'$ or $R_4'$ is hydrogen or $(C_1-C_6)$alkyl; $R_{11}$ is isopropyl when $R_{12}$ is hydrogen or $R_{11}$ is phenyl when $R_{12}$ is methyl; $R_{13}$ and $R_{14}$ are selected from hydrogen, $(C_1-C_6)$alkyl or hydroxyl; $R_{15}$ is hydrogen or $(C_1-C_6)$alkyl; $R_{16}$ is hydrogen or $(C_1-C_6)$alkyl; P is $(C_1-C_6)$alkyl, arylmethyl, substituted cyclohexyl or substituted oxazalone.

Scheme I

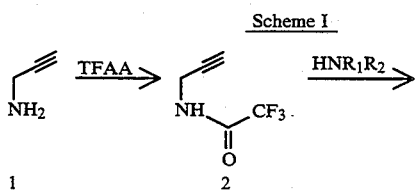

-continued
Scheme I

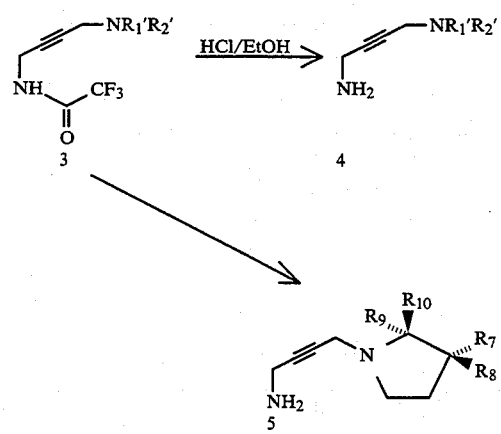

SCHEME I

In accordance with Scheme I, the diamines of general formula 4 and 5 are prepared by a modification of previously described methods [U.Swenson, U. Hacksell, R. Dahlboom. Acta Pharm. Suec., (1978), 15, 67; H. Bittiger, J. Heid, U.S. Pat. No. 3,354,178 (1967)]. The advantage, over the published procedures, is the mild conditions used to remove the trifluoroacetamide protecting group.

Propargylamine is treated with trifluoroacetic acid anhydride in a solvent such as diethyl ether, tetrahydrofuran or methylene chloride to afford trifluoroacetamide 2. Compound 2 is reacted with paraformaldehyde, acetic or propanoic acid, cuprous halide and a secondary amine such as pyrrolidine, dimethylamine, piperidine, (R)-3-acetoxypyrroldine or (S)-2-[[(1,1-dimethylethyl)dimethylsilyl]oxy]methylpyrrolidine in a ethereal solvent such as diethyl ether, tetrahydrofuran or dioxane at the reflux temperature of the solvent to give the amine of general formula 3. A compound of general formula 3 is reacted in an alcohol solvent such as methanol, ethanol or isopropanol containing a mineral acid to produce a diamine of general formula 4. When compounds of general formula contain an acid labile group, such as (S)-2-[[(1,1-dimethylethyl)dimethylsilyl]oxy]methylpyrrolidine, treatment with sodium borohydride in an alcohol solvent gives diamines of general formula 5.

Scheme II

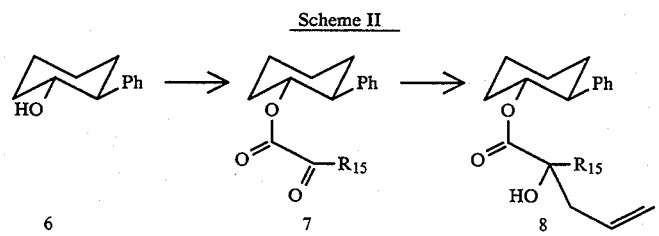

-continued
Scheme II

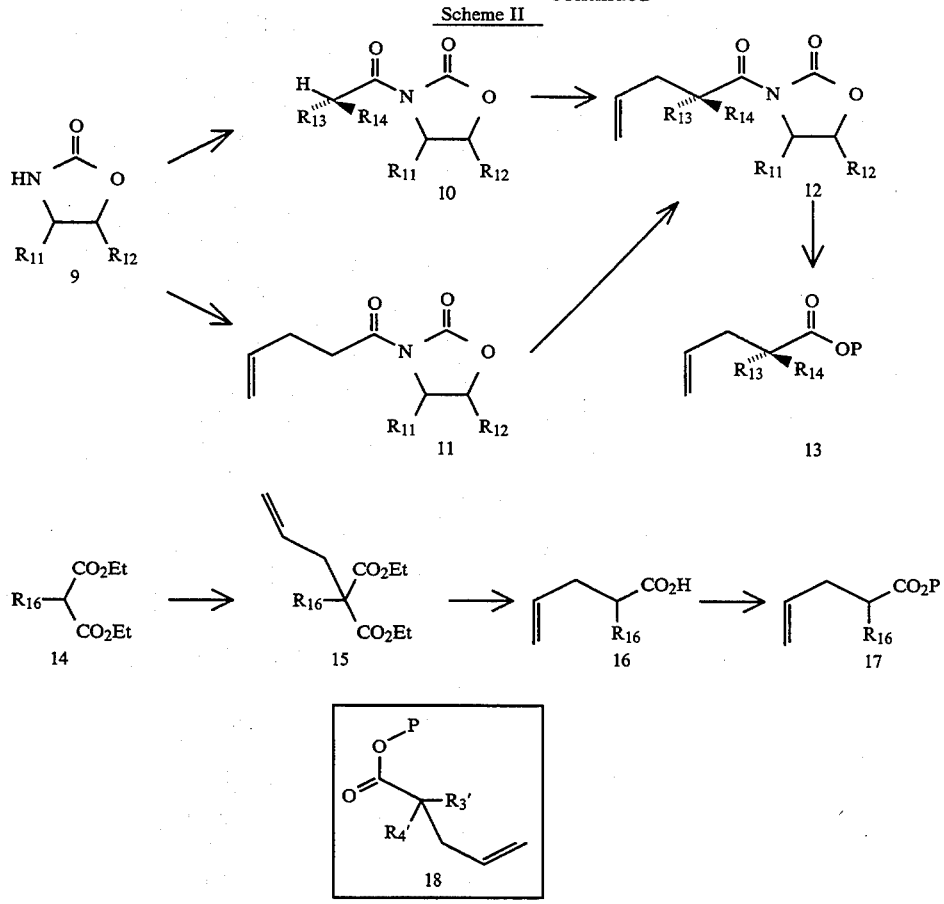

SCHEME II

In accordance with Scheme II, ester 8, wherein $R_{15}=(C_1-C_6)$alkyl, is prepared by the procedure of J. K. Whitesell et al., J. Org. Chem., 1989,54,2258. Ester 8 wherein $R_{15}$=hydrogen is prepared by the procedure of J. K. Whitesell et al., Tetrahedron, 1986, 42,2993.

Phenylcyclohexanone, in the racemic or optically active form (Chima, 1986, 40,318, Organic Synthesis, 1990, Vol 69, 1) is reacted with an α-ketoacid, such as pyruvic acid, in an inert solvent, such as benzene or toluene, in the presence of a catalytic amount of p-toluenesulfonic acid. Water is removed by azeotropic distillation to give a compound of general formula 7 wherein $R_{15}=(C_1-C_6)$alkyl. A compound of formula 7 is reacted with allyltrimethylsilane in the presence of stannic chloride in an inert solvent, such as methylene chloride, at −78° C. to give a compound of general formula 8.

Compounds of general formula 13 are optically active, wherein one of $R_{13}$ or $R_{14}$ =$(C_1-C_6)$alkyl and the other one is hydrogen, are prepared by the procedure of D. A. Evans et.al., J. Am. Chem. Soc.,1982, 104,1737.

A compound of general formula 9 is reacted with a lower alkyllithium reagent in an ether solvent, such as diethyl ether or tetrahydrofuran, at −78° C. followed by the addition of a $(C_2-C_8)$alkylcarboxylic acid chloride to give compounds of general formula 10. Alternatively, a compound of the general formula 9 is reacted with a lower alkyllithium reagent in an ether solvent, such as diethyl ether or tetrahydrofuran, at −78° C. followed by the addition of a 4-pentenoic acid chloride to give compounds of general formula 11. Reacting compounds of general formula 10 with a lower alkyllithium reagent, such as n-butyllithium or t-butyllithium, in an inert solvent, such as diethyl ether or tetrahydrofuran, at −78° C.; followed by the addition of a 2-propenyl halide and warming to −20° C. gives products of general formula 12. Alternately, reacting compounds of general formula 11 with a lower alkyllithium reagent, such as n-butyl- lithium or t-butyllithium, in an inert solvent, such as diethyl ether or tetrahydrofuran, at −78° C.; followed by the addition of a $(C_1-C_6)$alkyl halide and warming to −20° C. gives compounds of general formula 12. The addition of compounds of general formula 12 to a solution of a $(C_1-C_6)$alkyl alcohol or phenylmethyl alcohol and an alkyllithium reagent in an ether solvent, such as diethyl ether or tetrahydrofuran, at 0° C. gives compounds of general formula 13.

Compounds of general formula 17, wherein $R_{16}=(C_1-C_6)$alkyl and the other is hydrogen, are prepared by the procedure of A. V. Rama Rao et. al., Tetrahedron Letters, 1988, 29, 2069.

The dialkyl ester of $(C_1-C_6)$alkyl malonate 14 is treated, with an alkali metal alkoxide and subsequently reacted with a 2-propenyl halide, such as allylbromide, to give the disubstituted malonate ester 15. Ester 15 is subjected to saponification, using potassium hydroxide in a $(C_1-C_6)$alkyl alcohol, such as ethyl alcohol; followed by acidification, with a mineral acid; and decarboxylation by distillation to give the racemic acid 16. Reacting compound 15 with thionyl chloride or oxalyl chloride; followed by the addition of a $(C_1-C_6)$ alkyl alcohol, such as ethyl alcohol, or an arylmethyl alcohol, such as benzyl alcohol, gives the racemic ester 17.

As cited in the reference, the racemic acid may be resolved by reacting the product of treatment with thionyl chloride or oxalyl chloride with a resolving agent, such as L-phenylalaninol.

Compounds 8, 13 and 17 are of general formula 18, where P is as previously described.

by reacting the free hydroxyl with a trialkylsilyl chloride, such as t-butyldimethylsilyl chloride, and a trialkylamine, such as triethylamine, in an inert solvent, such as methylene chloride, before the compound is treated with cyanogen bromide. A compound of general formula 22 is treated with a secondary amine, such as pyrrolidine, dimethylamine, piperidine, (R)-3-acetoxypyrrolidine, (R)-[[(1,1-dimethylethyl)dimethylsilyl]oxy]-

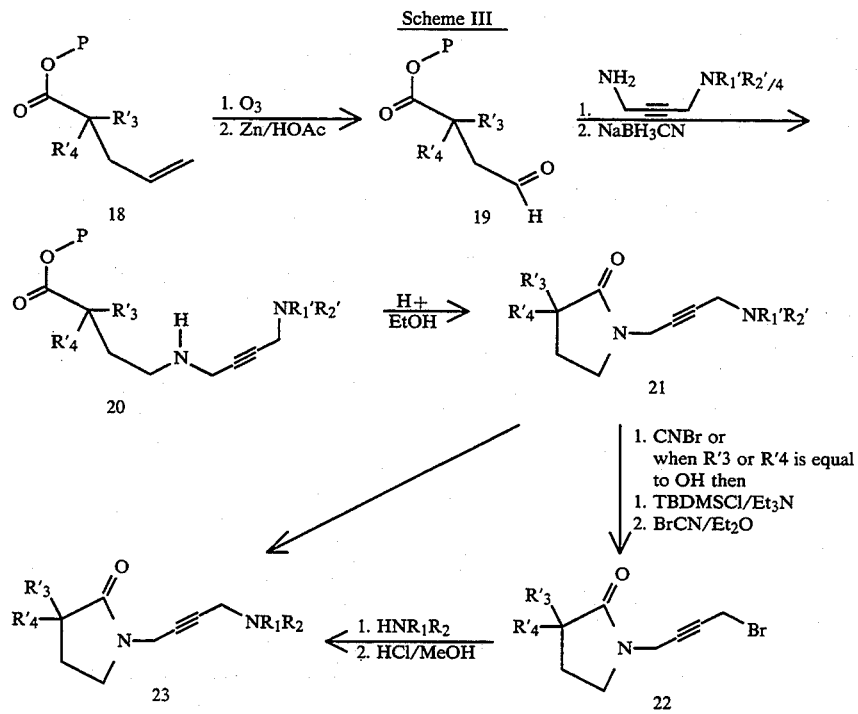

SCHEME III

In accordance with Scheme III compounds of general formula 18 prepared in accordance with Scheme II are reacted with compounds of general formulas 4, 5 prepared in accordance with Scheme I to ultimately yield the compounds of the present invention. Accordingly, compound of general formula 18 is treated with a stream of ozone at −78° C. in methylene chloride or a (C$_1$-C$_6$)alcohol, such as methyl alcohol or ethyl alcohol. The resulting solution is treated with a reducing agent, like a thioether, such as dimethylsulfide, a phosphine, such as triphenylphosphine, or zinc and acetic acid, to obtain an aldehyde of the general formula 19. An aldehyde of general formula 19 is reacted with a diamine of general formula 4 or 5 prepared as in Scheme I and sodium cyanoborohydride, in an alcohol solvent, such as methyl alcohol or ethyl alcohol containing a (C$_1$-C$_6$)alkylcarboxylic acid or a strong mineral acid to maintain an acidic pH, to give an aminoester of general formula 20. A compound of general formula 20 is converted to a lactam of general formula 21 by stirring at room temperature or heating at the reflux temperature of the alcohol solvent, such as methyl alcohol or ethyl alcohol, in the presence of an alkalimetal carbonate.

A compound of general formula 21, wherein R$_3$' or R$_4$' is not hydroxyl, is reacted at room temperature with cyanogen bromide in an ether solvent, such as diethyl ether, to give a compound of general formula 22. When a compound of general formula 21 contains a free hydroxyl, (i.e., R$_3$' or R$_4$'=hydroxyl), it is necessary to protect the hydroxyl group, for example as a silyl ether, pyrrolidine or (S)-2-[[[(1,1-dimethyethyl)dimethylsilyl]oxy]methyl]pyrrolidine to give a compound of general formula 23, where the protecting groups are retained. Removal of the silyloxy protecting group is achieved by treatment of the silylether with mineral acid or fluoride ion in an alcohol solvent. A compound of general formula 21 can be converted to a compound of general formula 23 using the procedures described in U.S. Pat. No. 4,937,235.

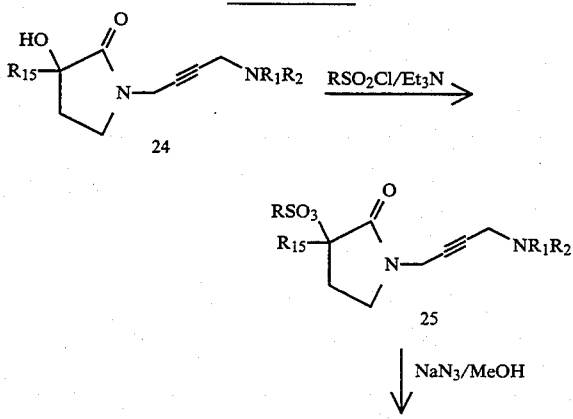

-continued
Scheme IV

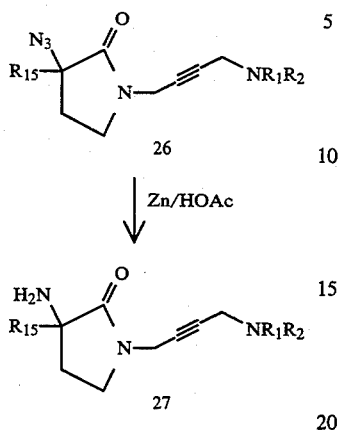

SCHEME IV

In accordance with Scheme IV, the preparation of the compounds of the present invention wherein $R_3$ or $R_4$ are amino or azido are described. In the foregoing Scheme IV, Compound 24 is a subset of compound 23, where $R_3'$ and $R_4'$ are independently selected from hydroxyl or $R_{15}$, wherein $R_{15}$ is $(C_1-C_6)$alkyl or hydrogen. Where $R_{15}$ is hydrogen, the compounds may be prepared as in Scheme III or as described in U.S. Pat. No. 4,937,235.

In accordance with Scheme IV, a compound of general formula 24 is reacted with an alkyl or arylsulfonyl chloride in the presence of an amine base such as pyridine or triethylamine; in an ether or a chlorohydrocarbon solvent at 0° C. (∓5° C.), to produce a compound of general formula 25. Treatment of compound 25 with an alkali metal azide, in an alcohol or a polar aprotic solvent such as dimethylformamide, at from room temperature to the reflux temperature of the solvent, gives a compound of general formula 26. Compound 26 is treated with a reducing agent, such as zinc in acetic acid or wet triphenylphosphine, to give a compound of general formula 27.

Scheme V

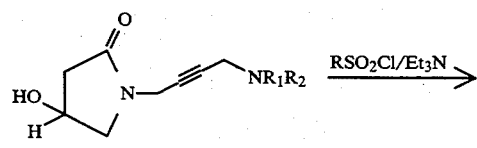

-continued
Scheme V

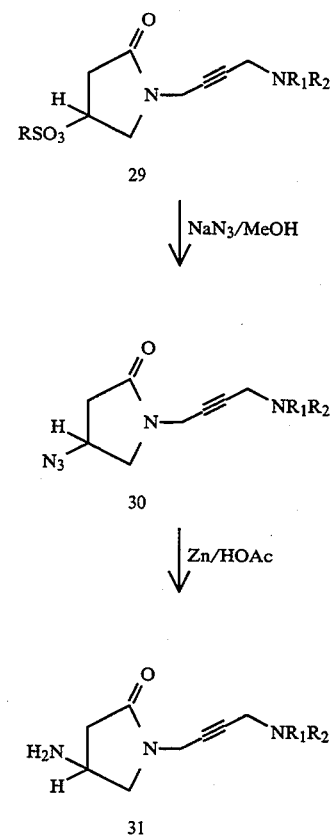

In accordance with Scheme V, the preparation of the compounds of the present invention wherein $R_5$ or $R_6$ are amino or azido is described. Accordingly, a compound of general formula 28, prepared by the methods described in U.S. Pat. No. 4,937,235, is reacted with an alkyl or arylsulfonyl chloride in the presence of an amine base such as pyridine or triethylamine, in an ether or a chlorohydrocarbon solvent at 0° C. (±5° C.) to produce a compound of general formula 29. Treatment of compound 29 with an alkali metal azide, in an alcohol or a polar aprotic solvent such as dimethylformamide, at from room temperature to the reflux temperature of the solvent, gives a compound of general formula 30. Compound 30 is treated with a reducing agent, such as zinc in acetic acid or wet triphenylphosphine, to give a compound of general formula 31.

SCHEME VI

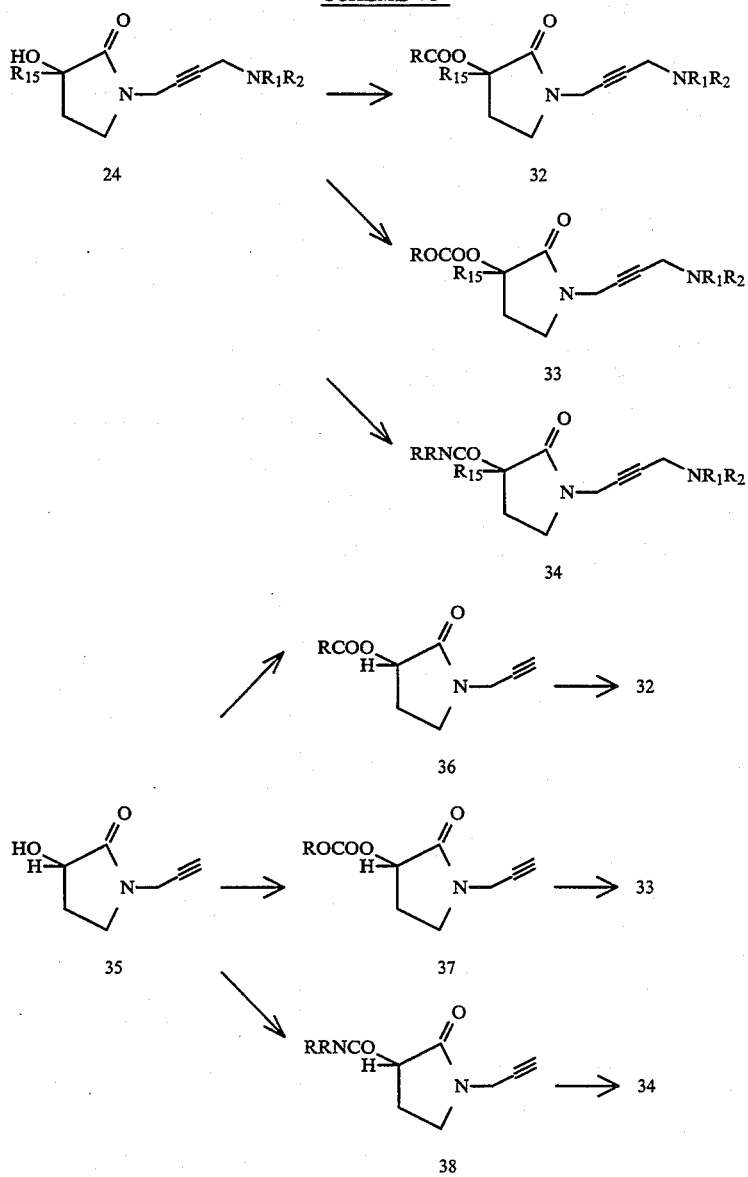

SCHEME VI

In accordance with Scheme VI, compound 24, prepared by methods described in U.S. Pat. No. 4,937,235, is reacted with a ($C_1$–$C_6$) or a ($C_7$–$C_{10}$)carboxylic acid anhydride or carboxylic acid halide in the presence of a base such as pyridine or triethylamine, in an ether or chlorohydrocarbon solvent, at 0° C. (±5° C.) to give a compound of general formula 32.

Compound 24 is reacted with a ($C_1$–$C_{10}$)alkylchloroformate in the presence of a base such as pyridine or triethylamine, in an ether or chlorohydrocarbon solvent, at 0° C. (±5° C.) to give a compound of general formula 33.

Compound 24 is reacted with a ($C_1$–$C_{10}$)alkylisocyanate or a ($C_1$–$C_{10}$)dialkylcarbamyl chloride in the presence of a base such as pyridine or triethylamine, in an ether or chlorohydrocarbon solvent, at 0° C. (±5° C.) to give a compound of general formula 34.

Alternatively, compound 35, prepared by the methods described in U.S. Pat. No. 4,937,235 is reacted with a ($C_1$–$C_6$) or a ($C_7$–$C_{10}$)carboxylic acid anhydride or a carboxylic acid halide in the presence of a base such as pyridine or triethylamine, in an ether or chlorohydrocarbon solvent at 0° C. (±5° C.) to give a compound of general formula 36.

Compound 35 is reacted with a ($C_1$–$C_{10}$)alkylchloroformate in the presence of a base such as pyridine or triethylamine, in an ether or chlorohydrocarbon solvent at 0° C. (±5° C.) to give a compound of general formula 37.

Compound 35 is reacted with a ($C_1$–$C_{10}$)alkylisocyanate or a ($C_1$–$C_{10}$)dialkylcarbamyl chloride in the presence of a base such as pyridine or triethylamine, in an ether or a chlorohydrocarbon solvent at 0° C. (±5° C.) to give a compound of general formula 38.

Compounds 36, 37 and 38 are reacted with paraformaldehyde, acetic acid, copper (I) or (II) chloride and a secondary amine as disclosed in $R_1'$ and $R_2'$ such as pyrrolidine, in an ether solvent, such as dioxane, in an inert atmosphere at the reflux temperature of the solvent, to give on basification, the corresponding compounds of general formula 32, 33 and 34 wherein $R_1$ and $R_2$ are selected from $R_1'$ and $R_2'$.

a $(C_1-C_6)$ or $(C_7-C_{10})$carboxylic acid anhydride or a carboxylic acid halide in the presence of a base, such as pyridine or triethylamine, in an ether or a chlorohydro-

SCHEME VII

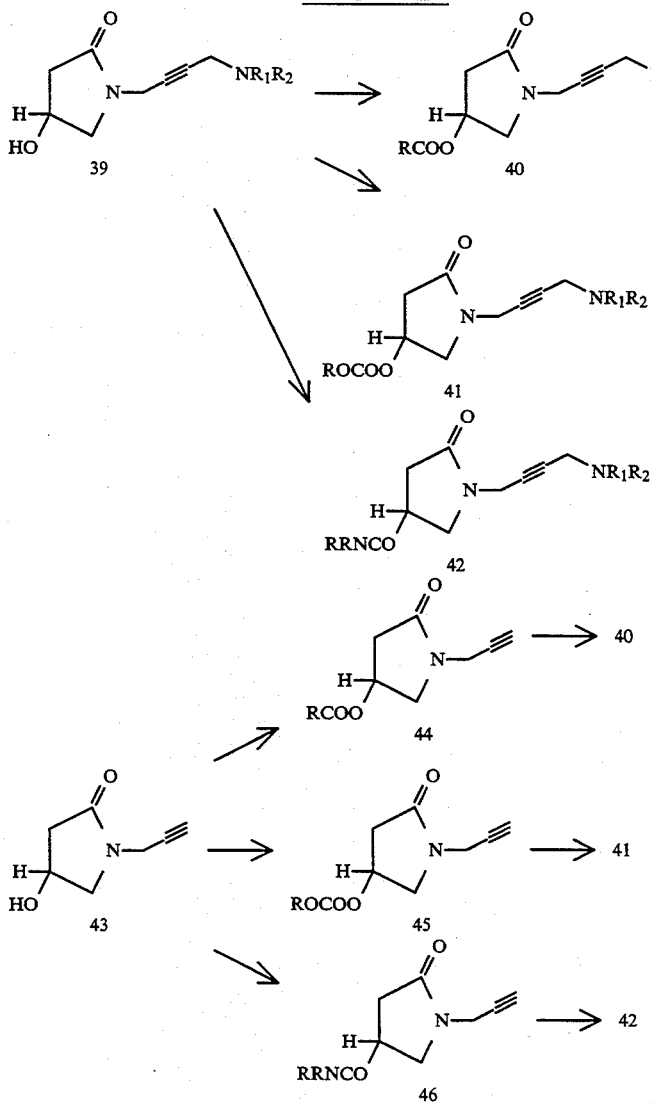

SCHEME VII

In accordance with Scheme VII, compound 39, prepared by methods described in U.S. Pat. No. 4,937,235, is reacted with a $(C_1-C_6)$ or $(C_7-C_{10})$ carboxylic acid anhydride or carboxylic acid halide in the presence of a base, such as pyridine or triethylamine, in an ether or chlorohydrocarbon solvent, at 0° C. (±5° C.) to give a compound of general formula 40.

Compound 39 is reacted with a $(C_1-C_{10})$alkylchloroformate in the presence of a base, such as pyridine or triethylamine, in an ether or chlorohydrocarbon solvent, at 0° C. (±5° C.) to give a compound of general formula 41.

Compound 39 is reacted with a $(C_1-C_{10})$alkylisocyanate or a $(C_1-C_{10})$dialkylcarbamyl chloride in the presence of a base, such as pyridine or triethylamine, in an ether or chlorohydrocarbon solvent, at 0° C. (±5° C.) to give a compound of general formula 42.

Alternatively, compound 43, prepared by the methods described in U.S. Pat. No. 4,937,235, is reacted with a $(C_1-C_6)$ or $(C_7-C_{10})$carboxylic acid anhydride or a carboxylic acid halide in the presence of a base, such as pyridine or triethylamine, in an ether or a chlorohydrocarbon solvent at 0° C. (±5° C.) to give a compound of general formula 44.

Compound 43 is reacted with a $(C_1-C_{10})$alkylchloroformate in the presence of a base, such as pyridine or triethylamine, in an ether or chlorohydrocarbon solvent at 0° C. (±5° C.) to give a compound of general formula 45.

Compound 47 is reacted with a $(C_1-C_{10})$alkylisocyanate or a $(C_1-C_{10})$dialkylcarbamyl chloride in the presence of a base, such as pyridine or triethylamine, in an ether or a chlorohydrocarbon solvent at 0° C. (±5° C.) to give a compound of general formula 44.

Compounds 44, 45 and 46 are reacted with paraformaldehyde, acetic acid, copper (I) or (II) chloride and a secondary amine as disclosed in $R_1'$ and $R_2'$ such as pyrrolidine, in an ether solvent, such as dioxane, in an inert atmosphere at the reflux temperature of the solvent, to give on basification, the corresponding compounds of general formula 40, 41 and 42 wherein $R_1$ and $R_2$ are selected from $R_1'$ and $R_2'$.

The compounds of this invention are tested for cholinergic activity according to the following procedures.

[$^3$H] Quinuclidinyl Benzilate Binding Assay

This assay is utilized in conjunction with the $^3$H-Cis-methyldioxolane binding assay to evaluate antagonist and high affinity agonist binding properties of CNS cholinergic agents. The procedure was adapted from Watson, M., Yamamura, H. I., and Roeske, W. R., J. Pharmacol. Exp. Ther. 237:411-418 (1986) and Watson, M., Roeske, W. R., and Yamamura, H. I., J. Pharmacol. Exp. Ther. 237:419-427 (1986).

Tissue Preparation:

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with ice-cold NaKPB for use in the assay. The final protein content per 2.0 ml of incubation mixture is 0.1 mg.

Dilution of Compounds:

A stock solution of Atropine is prepared at 0.2 mM to define non-specific binding (1 μM final conc). Test compounds are prepared at 40 mM (final conc 1 mM) in buffer (if water soluble) or in absolute ethanol—1N HCl (1:1, v/v) and serially diluted to the desired concentrations. In general, dose-response profiles are examined between 1 mM and 1 pM final concentrations.

Preparation of $^3$H-QNB:

H-QNB (NEN, NET-656; specific activity=30.0 Ci/mmol) is diluted to 5 nM, with NaPB (final concentration=0.25 nM activity 18,000 cpm at a counting efficiency of 55%).

H-QNB Binding Assay:

A typical protocol is outlined below:

| Tube No. | ID* | Buffer μL | Atropine μL | Test Compound μL | $^3$H-QNB μL | Tissue ml |
|---|---|---|---|---|---|---|
| 1-2 | Total | 50 | — | — | 100 | 1.85 |
| 3-4 | NS | 40 | 10 | — | " | " |
| 5-6 | 4e-11 | — | — | 50 | " | " |
| 7-8 | 4e-10 | — | — | " | " | " |
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | " | " | " |
| 23-24 | 4e-02 | — | — | " | " | " |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total—NS (non-specific). The percent inhibition of specific binding is then calculated and the Ki values computed using either the LIGAND or LUNDON software packages for competition binding. The results of this test on representative compounds of this invention appear in Table I.

[$^3$H]-Cis-methyldioxolane Binding Assay (High Affinity)

This assay is utilized in conjunction with $^3$H-QNB binding to evaluate high affinity agonist binding and antagonist properties of CNS cholinergic agents. The procedure was adapted from Vickroy, T. W., Roeske, W. R, and Yamamura, H. I, J. Pharmacol. Exp. Ther. 229: 747-755 (1984). This is a rapid filtration assay that is set up to label only the high affinity agonist conformation of the muscarinic cholinergic receptor.

Tissue Preparation:

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with ice-cold NaKPB for use in the assay. The final protein content per 2.0 ml of incubation mixture is 0.1 mg.

Dilution of Compounds:

A stock solution of Atropine is prepared at 0.2 mM to define non-specific binding (1 μM final conc). Test compounds are prepared at 40 mM (final conc 1 mM) in buffer (if water soluble) or in absolute ethanol—1N HCl (1:1, v/v) and serially diluted to the desired concentrations. In general, dose-response profiles are examined between 1 mM and 1 pM final concentrations.

Preparation of 3H-CD:

$^3$H-CD (NEN, NET-647; specific activity=55.5 Ci/mmol) is diluted to 20 nM with NaPB (final conc=1.0 nM, activity ~75,000 cpm at a counting efficiency of 55%).

Technical Notes:

$^3$H-CD adheres readily to both glass and plastic surfaces. To eliminate this problem (and the chance for introducing artifacts into the results), stock vials, pipette tips and all glass tubes are routinely treated with Prosil-28, a siliconizing agent, and oven dried prior to use in an assay. Additionally, the GF/B glass fiber filters are pre-soaked in an aqueous polyethylenimine (PEI) solution (0.1%, pH 7.0) prior to use.

All points in the inhibition curve (including total and non-specific binding)are always measured on single PEI treated filter strips to minimize filter-to-filter variability. (See Bruns, R. F., et al. Anal. Biochem. 132:74–81 (1983) for the use of PEI treated filters in filtration receptor assays).

The $^3$H-CD is prepared fresh in buffer just prior to use in the assay to avoid possible decomposition. It should be kept on an ice bath after dilution in buffer.

$^3$H-CD Binding Assay:

A typical protocol is outlined below:

| Tube No. | ID* | Buffer μL | Atropine μL | Test Compound μL | $^3$H-QNB μL | Tissue ml |
|---|---|---|---|---|---|---|
| 1-2 | Total | 50 | — | — | 100 | 1.85 |
| 3-4 | NS | 40 | 10 | — | " | " |
| 5-6 | 4e-11 | — | — | 50 | " | " |
| 7-8 | 4e-10 | — | — | " | " | " |
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | " | " | " |
| 23-24 | 4e-02 | — | — | " | " | " |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total—NS (non-specific). The percent inhibition of specific binding is then calculated and the Ki values computed using either the LIGAND or LUNDON software packages for competition binding. The results of this test on representative compounds of this invention appear in Table I.

TABLE 1

In vitro Binding Data

| Compound | $^3$H-QNB Ki uM | $^3$H-CD Ki uM |
|---|---|---|
| 2,2,2-Trifluoro-N-[4(1-pyrrolidinyl)-2-butynyl]acetamide monohydrochloride | 18.5 | 8.88 |
| N-[4-Dimethylamino)-2-butynyl]-2,2,2-trifluoroacetamide monohydrochloride | >100 | 6.10 |
| N-[(4-Diethylamino)-2-butynyl]-2,2,2-trifluoroacetamide monohydrochloride | >100 | 4.07 |
| (S)-N-[4-[2-[[[(1,1-Dimethylethyl]-dimethylsilyl]oxy]methyl]-1-pyrrolidinyl]-2-butynyl]-2,2,2-trifluoroacetamide | >100 | 41.4 |
| 4-(1-Pyrrolidinyl)-2-butyn-1-amine dihydrochloride | >100 | 13.0 |
| N,N-Dimethyl-2-butyne-1,4-diamine dihydrochloride | >100 | 20.5 |
| N,N-Diethyl-2-butyne-1,4-diamine dihydrochloride | >100 | >100 |
| Racemic-1-[4-Dimethylamino)-2-butynyl]-3-hydroxy-3-methyl-2-pyrrolidinone | >100 | >100 |
| Racemic-3-Hydroxy-3-methyl-1-[4-(1-pyrrolidinyl)-2-butynyl]-2-pyrrolidinone | 8.6 | 5.70 |
| Racemic 1-[4-(1-Dimethylamino)-2-butynyl]-3-methyl-2-pyrrolidinone | 21 | 0.41 |
| Racemic 1-[4-(1-Diethylamino)-2-butynyl]-3-methyl-2-pyrrolidinone | 6.0 | 5.1 |
| (S)-1-[4-(Dimethylamino)-2-butynyl]-3-methyl-2-pyrrolidinone | 35.5 | 0.68 |
| (R)-1-[4-(Dimethylamino)-2-butynyl]-3-methyl-2-pyrrolidinone | 7.7 | 0.073 |
| Racemic 1-[4-(1H-imidazol-1-yl)-2-butynyl]-3-methyl-2-pyrrolidinone | 6.7 | 0.057 |
| Racemic 1-[4-(l-azetidinyl)-2-butynyl-3-methyl-2-pyrrolidinone | 2.0 | 0.054 |
| [R-[(R*, R* and R*, S*)]]-1-[4-[2-[[[(1,1-Dimethylethyl)dimethylsilyl]methyl]-1-pyrrolidinyl]-2-butynyl]-3-methyl-2-pyrrolidinone | 2.5 | 5.6 |
| [R-(R*, R* and R*, S*)]-1-[4-[3-[[(1,1-Dimethylethyl)dimethylsilyl]oxy]-1-pyrrolidinyl]-2-butynyl]-3-methyl-2-pyrrolidinone | >100 | >100 |
| (S)-1-[4-(Diethylamino)-2-butynyl]-3-[[(1,1-dimethylethyl)dimethylsilyl]-oxy]-2-pyrrolidinone | 7.6 | 15.4 |
| (S)-1-[4-(l-Azetidinyl)-2-butynyl]-3-[[(1,1-dimethylethyl)dimethylsilyl]-oxy]-2-pyrrolidinone | 5.8 | 5.6 |
| (R)-1-[4-(1-Azetidinyl)-2-butynyl]-3-[[(1,1-dimethylethyl)dimethylsilyl]-oxy]-2-pyrrolidinone | >100 | >100 |
| (S)-3-[[(1,1-Dimethylethyl)dimethyl-silyl]oxy]-1-[4-(1H-imidazol-1-yl)-2-butynyl-2-pyrrolidinone | >100 | 24.3 |
| (R)-3-[[(1,1-Dimethylethyl)dimethyl-silyl]oxy]-1-[4-(1H-imidazol-1-yl)-2-butynyl]-2-pyrrolidinone | >100 | 14.0 |

TABLE 1-continued

| In vitro Binding Data | | |
|---|---|---|
| Compound | $^3$H-QNB Ki uM | $^3$H-CD Ki uM |
| (S)-3-Hydroxy-1-[4-(1H-imidazol-1-yl)-2-butynyl]-2-pyrrolidinone | >100 | 0.12 |
| 1-[4-(1H-Imidazol-1-yl)-2-butynyl]-3-hydroxy-2-pyrrolidinone | >100 | 2.0 |
| (S)-1-[4-(Dimethylamino)-2-butynyl]-3-[[(1,1-Dimethylethyl)dimethylsilyl]oxy]-2-pyrrolidinone | 14.3 | 18.2 |
| (S)-1-(4-(Dimethylamino)-2-butynyl]-3-hydroxy-2-pyrrolidinone | 26.9 | 0.043 |
| (R)-1-[4-(Dimethylamino)-2-butynyl]-3-hydroxy-2-pyrrolidinone | 104.7 | 0.54 |
| (S)-3-[[(1,1-Dimethylethyl)dimethylsilyl]oxy]-1-[4-(1-pyrrolidinyl)-2-butynyl]-2-pyrrolidinone | 2.7 | 3.0 |
| (S)-3-Hydroxy-1-[4-(1-pyrrolidinyl)-2-butynyl]-2-pyrrolidinone | 1.7 | 0.007 |
| (R)-3-Hydroxy-1-[4-(1-pyrrolidinyl)-2-butynyl]-2-pyrrolidinone | 3.4 | 0.125 |
| (S)-3-Hydroxy-1-[4-[(2-hydroxyethyl)methylamino]-2-butynyl]-2-pyrrolidinone | >100 | 1.82 |
| (R)-3-Hydroxy-1-[4-[(4-hydroxybutyl)methylamino]-2-butynyl]-2-pyrrolidinone | >100 | 1.45 |
| [R-(R*, S*)]-3-(Acetyloxy)-1-[4-[2-[[[(1,1-dimethylethyl)dimethylsilyl]oxy]methyl]-1-pyrrolidinyl]-2-butynyl]-2-pyrrolidinone | 500 | 1.7 |
| [S-(R*, R*)]-3-(Acetyloxy)-1-[4-[2-[[[(1,1-dimethylethyl)dimethylsilyl]oxy]methyl]-1-pyrrolidinyl]-2-butynyl]-2-pyrrolidinone | 2.6 | 0.079 |
| [S-(R*, S*)]-3-(Acetyloxy)-1-[4-[2-[[[(1,1-dimethylethyl)dimethylsilyl]oxy]methyl]-1-pyrrolidinyl]-2-butynyl]-2-pyrrolidinone | >100 | 4.2 |
| [R-(R*, R*)]-3-Acetyloxy-1-[4-[2-[[[(1,1-dimethylethyl)dimethylsilyl]oxy]methyl]-1-pyrrolidinyl]-2-butynyl]-2-pyrrolidinone | >100 | 10.1 |
| (S)-3-(Acetyloxy)-1-[4-[2-(hydroxyethyl)methylamino]-2-butynyl]-2-pyrrolidinone | >100 | 16.2 |
| (R)-3-(Acetyloxy)-1-[4-[(2-hydroxyethyl)methylamino]-2-butynyl]-2-pyrrolidinone | >100 | 28.3 |
| (S)-3-(Acetyloxy)-1-[4-[(4-hydroxybutyl)methylamino]-2-butynyl]-2-pyrrolidinone | >100 | 8.21 |
| [R-(R*, S*)]-1-[4-[2-[[[(1,1-Dimethylethyl)dimethylsilyl]oxy]methyl]-1-pyrrolidinyl]-2-butynyl]-3-hydroxy-2-pyrrolidone | 0.5 | 0.47 |
| [S-(R*, R*)]-1-[4-[2-[[[(1,1-Dimethylethyl)dimethylsilyl]oxy]methyl]-1-pyrrolidinyl]-2-butynyl]-3-hydroxy-2-pyrrolidinone | 0.4 | 0.14 |
| [S-(R*, S*)]-1-[4-[2-[[[(1,1-Dimethylethyl)dimethylsilyl]oxy]methyl]-1-pyrrolidinyl]-2-butynyl]-3-hydroxy-2-pyrrolidinone | 198 | 1.7 |
| [R-(R*, R*)]-1-[4-[2-[[[(1,1-Dimethylethyl)dimethylsilyl]oxy]methyl]-1-pyrrolidinyl]-2-butynyl]-3-hydroxy-2-pyrrolidinone | >100 | 4.2 |
| (R)-3-Hydroxy-1-[4-[(2-hydroxyethyl)methylamino]-2-butynyl]-2-pyrrolidinone | >100 | 1.80 |
| (S)-3-Hydroxy-1-[4-[(4-hydroxybutyl)methylamino]-2-butynyl]-2-pyrrolidinone | >100 | 1.3 |
| [S-(R*, S*)]-3-Hydroxy-1-[4-(2-(hydroxymethyl)-1-pyrrolidinyl]-2-butynyl]-2-pyrrolidinone | >100 | 2.60 |
| [S-(R*, R*)]-3-Hydroxy-1-[4-[2-(hydroxymethyl)-1-pyrrolidinyl]-2-butynyl]-2-pyrrolidinone | >100 | 34.3 |
| (S)-3-(Methylthio)-1-[4-(1-pyrrolidinyl)-2-butynyl]-2- | 53 | 1.04 |

TABLE 1-continued

| Compound | In vitro Binding Data | |
|---|---|---|
| | $^3$H-QNB Ki uM | $^3$H-CD Ki uM |
| pyrrolidinone | | |
| (R)-3-(Methylithio)-1-[4-(1-pyrrolidinyl)-2-butynyl]-2-pyrrolidinone | 3.6 | 1.4 |
| (S)-1-[4-(Dimethylamino)-2-butynyl]-3-(methylthio)-2-pyrrolidinone | >100 | 6.4 |
| (R)-1-[4-(Dimethylamino)-2-butynyl]-3-(methylthio)-2-pyrrolidinone | 108 | 6.1 |
| (S)-N,N,N-Trimethyl-4-[3-(methylthio)-2-oxo-1-pyrrolidinyl]-2-butyn-1-aninium iodide | 1.8 | 0.31- |
| (S)-3-Azido-1-[4-(1-pyrrolidinyl)-2-butynyl]-2-pyrrolidinone | 3.14 | 0.16 |
| (S)-3-Amino-1-[4-(1-pyrrolidinyl)-2-butynyl]-2-pyrrolidinone dihydrochloride | 73.6 | 0.41 |
| (R)-3-Azido-1-[4-(1-pyrrolidinyl)-2-butynyl]-2-pyrrolidinone | 28 | 0.21 |
| (R)-3-Amino-1-[4-(1-pyrrolidinyl)-2-butynyl]-2-pyrrolidinone dihydrochloride | 6.1 | 0.35 |
| (S)-3-Azido-1-[4-(dimethylamino)-2-butynyl]-2-pyrrolidinone | >100 | 0.63 |
| (R)-3-Azido-1-[4-(dimethylamino)-2-butynyl]-2-pyrrolidinone | >100 | 0.50 |
| (S)-4-(3-Azido-2-oxo-1-pyrrolidinyl)-N,N,N-trimethyl-2-butyn-1-aminium iodide | 1.6 | 0.045 |
| (R)-4-(3-Azido-2-oxo-1-pyrrolidinyl)-N,N,N-trimethyl-2-butyn-1-aminium iodide | 0.8 | 0.039 |
| (S)-3-Amino-1-[4-(dimethylamino)-2-butynyl]-2-pyrrolidinone dihydrochloride | >100 | 2.6 |
| (R)-3-Amino-1-[4-(dimethylamino)-2-butynyl]-2-pyrrolidinone dihydrochloride | >100 | 0.89 |
| (S)-2-Methylpropanoic acid 1-[4-(dimethylamino)-2-butynyl]-2-oxo-3-pyrrolidinyl ester | 610 | ND |
| (S)-2,2-Dimethylpropanoic acid 1-[4-(dimethylamino)-2-butynyl]-2-oxo-3-pyrrolidinyl ester | 484 | 38.8 |
| (S)-Decanoic acid 1-[4-(dimethylamino)-2-butynyl]-2-oxo-3-pyrrolidinyl ester | 0.6 | 0.023 |
| (S)-Carbonic acid 1-[4-(dimethylamino)-2-butynyl]-2-oxo-3-pyrrolidinyl octyl ester | 10 | 0.306 |
| (S)-Carbonic acid 1-[4-(dimethylamino)-2-butynyl]-2-oxo-3-pyrrolidinyl]methyl ester | 15.1 | 2.16 |
| (S)-N,N,N-Trimethyl-4-[2-oxo-3-[(1-oxodecyl)oxy]-1-pyrrolidinyl-2-butyn-1-aminium iodide | 0.003 | 0.156 |
| (S)-N,N,N-Trimethyl-4-[3-(2-methyl-1-oxopropoxy)-2-oxo-1-pyrrolidinyl]-2-butyn-1-aminium iodide | 64.3 | 6.96 |
| (S)-4-[3-(2,2-Dimethyl-1-oxopropoxy)-2-oxo-1-pyrrolidinyl]-N,N,N-trimethyl-2-butyn-1-aminium iodide | 478 | 7.80 |
| (S)-N,N,N-Trimethyl-4-[3-[[(octyloxy)carbonyl]oxy]-2-oxo-1-pyrrolidinyl]-2-butyn-1-aminium iodide | 0.1 | 0.013 |
| (S)-2-Methylpropanoic acid 2-oxo-1-[4-(1-pyrrolidinyl)-2-butynyl]-3-pyrrolidinyl ester | 7.2 | 0.162 |
| (S)-2,2-Dimethylpropanoic acid 2-oxo-1-[4-(1-pyrrolidinyl)-2-butynyl]-3-pyrrolidinyl ester | 4.6 | 0.37 |
| (S)-3-[[(Methylamino)carbonyl]oxy-1-(4-(1-pyrrolidinyl)-2-butynyl]-2-pyrrolidinone | 433 | >100 |
| (S)-Dimethylcarbamic acid 2-oxo-1-[4-(1-pyrrolidinyl)-2-butynyl]-3-pyrrolidinyl ester | 40.3 | 9.56 |
| (S)-Carbonic acid hexyl 2-oxo-1-[4-(1-pyrrolidinyl)-2-butynyl]-3-pyrrolidinyl ester | 1.7 | 0.015 |

TABLE 1-continued

In vitro Binding Data

| Compound | $^3$H-QNB Ki uM | $^3$H-CD Ki uM |
|---|---|---|
| (S)-Carbonic acid methyl 2-oxo-1-[4-(1-pyrrolidinyl)-2-butynyl]-3-pyrrolidinyl ester | 5.4 | 0.053 |
| (S)-Carbonic acid methyl 2-oxo-1-[4-(1-pyrrolidinyl)-2-butynyl]-3-pyrrolidinyl ester | 10.4 | 0.23 |
| (R)-Propanoic acid 2-methyl-1-[4-(dimethylamino)-2-butynyl]-2-oxo-3-pyrrolidinyl ester | 711 | 26.0 |
| (R)-2,2-Dimethylpropanoic acid 1-[4-(dimethylamino)-2-butynyl]-2-oxo-3-pyrrolidinyl ester | 404 | ND |
| (R)-Decanoic acid 1-[4-(dimethylamino)-2-butynyl]-2-oxo-3-pyrrolidinyl ester | >100 | 0.73 |
| (R)-Octylcarbamic acid 1-[4-(dimethylamino)-2-butynyl]-2-oxo-3-pyrrolidinyl ester | 32 | 1.43 |
| (R)-Carbonic acid 1-[4-(dimethylamino)-2-butynyl]-2-oxo-3-pyrrolidinyl methyl ester monohydrochloride | 52 | 3.07 |
| (R)-Carbonic acid 1-[4-(dimethylamino)-2-butynyl]-2-oxo-3-pyrrolidinyl octyl ester | 1.5 | 1.04 |
| (R)-N,N,N-Trimethyl-4-[3-(2-methyl-1-oxopropoxy)-2-oxo-1-pyrrolidinyl]-2-butyn-1-aminium iodide | 45 | 0.24 |
| (R)-4-[3-(2,2-Dimethyl-1-oxopropoxy)-2-oxo-1-pyrrolidinyl]-N,N,N-trimethyl-2-butyn-1-aminium iodide | >100 | 1.22 |
| (R)-4-[2-Oxo-3-[(1-oxodecyl)oxy]-1-pyrrolidinyl]-N,N,N-trimethyl-2-butyn-1-aminium iodide | 0.2 | 0.050 |
| (R)-N,N,N-Trimethyl-4-[3-[[(octylamino)carbonyl]oxy]-2-oxo-1-pyrrolidinyl]-2-butyn-1-aminium iodide | 0.5 | 0.49 |
| (R)-N,N,N-Trimethyl-4-[3-[[(octyloxy)carbonyl]oxy]-2-oxo-1-pyrrolidinyl]-2-butyn-1-aminium iodide | 0.2 | 0.010 |
| (R)-2-Methylpropanoic acid 2-oxo-1-[4-(1-pyrrolidinyl)-2-butynyl]-3-pyrrolidinyl ester | 87 | 0.135 |
| (R)-2,2-Dimethylpropanoic acid 2-oxo-1-[4-(1-pyrrolidinyl)-2-butynyl]-3-pyrrolidinyl ester | 10.2 | 0.50 |
| (R)-Decanoic acid 2-oxo-1-[4-(1-pyrrolidinyl)-2-butynyl]-3-pyrrolidinyl ester | 0.2 | 0.097 |
| (R)-Carbonic acid 2-oxo-1-[4-(1-pyrrolidinyl)-2-butynyl]-3-pyrrolidinyl phenymethyl ester | 1.4 | 0.11 |
| (R)-Octylcarbamic acid 2-oxo-1-[4-(1-pyrrolidinyl)-2-butynyl]-3-pyrrolidinyl ester | 0.2 | 0.24 |
| (R)-Carbonic acid octyl 2-oxo-1-[4-(1-pyrrolidinyl)-2-butynyl]-3-pyrrolidinyl ester | 0.1 | 0.076 |
| (R)-Carbonic acid methyl 2-oxo-1-[4-(1-pyrrolidinyl)-2-butynyl]-3-pyrrolidinyl ester | 27.3 | 0.35 |
| (S)-Decanoic acid 2-oxo-1-[4-(1-pyrrolidinyl)-2-butynyl]-4-pyrrolidinyl ester | 0.035 | 0.33 |
| (S)-Carbonic acid methyl 2-oxo-1-(4-(1-pyrrolidiny)-2-butynyl]-4-pyrrolidinyl ester | 1.8 | 0.85 |
| (S)-Octylcarbamic acid 2-oxo-1-[4-(1-pyrrolidinyl-2-butynyl]-4-pyrrolidinyl ester | 0.13 | 0.35 |

Those compounds which have $^3$H-CD and $^3$H-QNB Ki values of less than 100 μM are considered active. The compounds tested can be divided into 3 categories:
1. compounds which are products or therapeutic agents;
2. compounds which are a prodrug form of the products or therapeutic agents and 3. compounds which are reaction intermediates.

The term prodrug signifies a compound which is to some degree chemically and biochemically labile.

When the prodrug is metabolized in the body, the active product or therapeutic agent is released or unmasked.

The pharmaceutical preparations of the present invention may contain, for example, from about 0.5% up to about 90% of the active ingredient in combination with the carrier, more usually between 5% and 60% by weight.

The effective dosage of active ingredient employed may vary with the particular compound employed, the mode of administration, and the severity of the condition being treated. In general, however, satisfactory results are obtained when the compounds of the invention are administered at a daily dosage of from about 0.02 mg to about 100 mg/kg of patient body weight, preferably given in divided doses two to four times a day, or in sustained release form. For most patients, the total daily dosage is from about 1 mg to about 5,000 mg, preferably from about 1 mg to 20 mg. Dosage forms suitable for internal use comprise from about 0.25 to 5.0 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile water, polyethylene glycols, non-ionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, and antioxidants, e.g., vitiamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions of manufacture and storage and must be preserved against the contaminating action of microorganisms such as bacteria and fungi. The carrier can be a solvent or dispersion medium containing, for example, water ethanol, polyol (e.g., glycerol, propylene glycol, and liquid polyethylene glycol), suitable mixtures thereof, and vegetable oils.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

2,2,2-Trifluoro-N-2-propynylacetamide

To a stirring 0° C. solution of 15.0 g of propargylamine in 200 ml of methylene chloride is added, dropwise, a solution of 63.0 g of trifluoroacetic anhydride in 50 ml of methylene chloride. The reaction is stirred at room temperature for 1 hour followed by the addition of 100 ml of water. The mixture is washed with 150 ml of 1N hydrochloric acid and 150 ml of saturated sodium bicarbonate. The organic layer is dried, filtered and concentrated in vacuo. The residue is distilled under vacuum (0.2 mm Hg) at 40° C. to give 32.1 g of the desired product as a colorless oil.

EXAMPLE 2

2,2,2-Trifluoro-N-[4-(1-pyrrolidinyl)-2-butynyl]acetamide monohydrochloride

A mixture of 50.0 g of product from Example 1, 47.1 g of pyrrolidine, 24.9 g of paraformaldehyde, 50 ml of glacial acetic acid, 0.5 g of cuprous chloride and 500 ml of dry dioxane is heated at reflux temperature for 20 minutes. The reaction mixture is concentrated in vacuo and made basic to pH 10–11 with concentrated ammonium hydroxide. The aqueous layer is extracted with methylene chloride. The combined organic extracts are dried over sodium sulfate, filtered through a pad of diatomaceous earth and concentrated in vacuo. The residue is distilled under vacuum (0.3 mm Hg) at 110°–120° C. to give the desired product as a yellow oil. Eight grams of oil is dissolved in 1N methanolic hydrogen chloride. The resulting solid is collected and recrystallized from methyl alcohol/diethyl ether to give 1.7 g of the desired product as the monohydrochloride.

MP 125°–127° C.

Following the general procedure of Example 2 and using 2,2,2-trifluoro-N-2-propynylacetamide (Example 1), the products of Examples 3–5, found in Table II, are prepared.

TABLE II

| Example | Reactant | Product | MP °C./or $[\text{alpha}]_D^{26°}$ (methylene chloride) |
|---|---|---|---|
| 3 | Dimethylamine | N-[4-Dimethylamino)-2- | 112–114° |

TABLE II-continued

| Example | Reactant | Product | MP °C./or [alpha]$_D^{26°}$ (methylene chloride) |
|---|---|---|---|
| 4 | Diethylamine | N-[4-(Diethylamino)-2-butynyl]-2,2,2-trifluoroacetamide monohydrochloride | 111–112° |
| 5 | (S)-2-[[[1,1-(Dimethylethyl)-dimethylsilyl]oxy-methyl]-1-pyrrolidinyl]-2-butynyl]-2,2,2-trifluoroacetamide | (S)-N-[4-[2-[[[(1,1-Dimethylethyl]-dimethylsilyl]oxy]-methyl]-1-pyrrolidinyl]-2-butynyl]-2,2,2-trifluoroacetamide | [alpha]$_D^{26}$ = −41° |

EXAMPLE 6

4-(1-pyrrolidinyl)-2-butyn-1-amine dihydrochloride

A mixture of 50.0 g of product from Example 2 and 267 ml of 4N hydrochloric acid is heated at reflux temperature. After 2 hours, the progress of the reaction is checked by thin layer chromatography, 70 ml of concentrated hydrochloric acid is added and the mixture is heated at reflux temperature overnight. The reaction is concentrated in vacuo and the residue is washed with methylene chloride. The aqueous layer is cooled, made basic with 10N sodium hydroxide and extracted with methylene chloride. The combined organic extracts are dried over sodium sulfate, filtered and concentrated in vacuo to give 27.8 g of a dark oil. The oil is treated with 450 ml of 1N methanolic hydrogen chloride and concentrated in vacuo. The resulting solid is recrystallized from methyl alcohol/diethyl ether to give 31.2 g of the desired product as off-white crystals.

MP 192°–193° C.

Following the general procedure of Example 6, the products of Examples 7–8, found in Table III, are prepared.

TABLE III

| Example | Starting Material | Reactant | Product | MP °C. |
|---|---|---|---|---|
| 7 | Example 3 | Hydrochloric acid | N,N-Dimethyl-2-butyne-1,4-diamine dihydrochloride | 181–183° |
| 8 | Example 4 | Hydrochloric acid | N,N-Diethyl-2-butyne-1,4-diamine dihydrochloride | 149–150° |

EXAMPLE 9

(S)-4-[2-[[[(1,1-Dimethylethyl]dimethylsily]oxy]methyl]-1-pyrrolidinyl]-2-butyn-1-amine To a stirring solution of 5.76 g of product from Example 5 in 145 ml of tetrahydrofuran and 3 ml of water is added 5.76 g of sodium borohydride. The reaction is stirred at room temperature for 18 hours followed by concentration in vacuo to half volume. Saturated sodium chloride is added and the mixture is extracted with methylene chloride. The organic layer is concentrated in vacuo to give a viscous oil. The oil is purified by chromatography (alumina, grade 2.5, 1% methyl alcohol/methylene chloride) to give 1.92 g of the desired product as a colorless oil.

[α]$_D^{26°}$ = −56° (methyl alcohol, c=1.016%).

EXAMPLE 10

Racemic 1-[4-(Dimethylamino)-2-butynyl]-3-hydroxy-3-methyl-2-pyrrolidinone

A solution of 5.0 g of 2-phenylcyclohexanol, 8.25 g of pyruvic acid, 0.3 g of p-toluenesulfonic acid and 100 ml of toluene is heated at reflux temperature. A Dean-Stark trap is used to collect the water distillate. The reaction is cooled, washed with aqueous sodium bicarbonate, dried and the filtrate concentrated in vacuo. The residue is purified by column chromatography (silica gel, methylene chloride) to give 5.5 g of trans-2-phenylcyclohexylpyruvate.

To a −78° C. solution of 15 g of trans-2-phenylcyclohexylpyruvate in 400 ml of methylene chloride is added, dropwise via syringe, 9.0 g of stannic chloride. The solution is stirred for 10 minutes followed by the addition of 25 ml of allyltrimethylsilane in 15 ml of methylene chloride. The reaction is stirred at −78° C. for 1 hour. Eighteen ml of triethylamine is added and the mixture allowed to warm to room temperature. Twenty-five ml of water and 10 g of diatomaceous earth is added and the mixture filtered through a pad of diatomaceous earth. The organic layer is washed with water, dried and concentrated in vacuo. The residue is purified by chromatography (silica gel, 10% ethyl acetate/petroleum ether) to give 16 g of trans-2-phenylcyclohexyl-2-hydroxy-2-methyl-4-pentenoate.

A stream of ozone is passed through a solution of 5.0 g of trans-2-phenylcyclohexyl-2-hydroxy-2-methyl-4-pentenoate in 150 ml of methylene chloride until a blue color persists. The blue color is discharged with a stream of argon. Two ml of dimethylsulfide is added and the solution allowed to warm to room temperature. The solution is concentrated to approximately 75 ml, washed with saturated sodium chloride, dried and concentrated in vacuo. The residue is diluted with 100 ml of methyl alcohol and successively treated with 3.2 g of sodium acetate, 10 ml of acetic acid and 3.0 g of N,N-dimethyl-2-butyne-1,4-diamine hydrochloride. The resulting reaction mixture is stirred at room temperature for 10 minutes. One and one-half grams of sodium cyanoborohydride is added, in portions, over the next 2 hours and the reaction is stirred overnight at room temperature. The mixture is concentrated in vacuo, partitioned between methylene chloride and saturated aqueous sodium carbonate, and the layers separated. The organic layer is dried and concentrated in vacuo. The residue is a mixture of the product and its ring open form 4-[[4-(dimethylamino)-2-butynyl]amino]-2-methylbutanoic acid ethyl ester. The oil which is a mixture of the product and its ring open form, 0.030 g of p-toluenesulfonic acid and 150 ml of ethyl alcohol is heated at reflux temperature for 36 hours. The solution is concentrated in vacuo and the residue purified by chromatography (alumina, 1–5% methyl alcohol/methylene chloride) to give 1.4 g of the desired product as a waxy solid.

MP 58°–59° C.

CI-MS: m/z 211 (M+H+).

EXAMPLE 11

Racemic 3-hydroxy-3-methyl-1-[4-(1-pyrrolidinyl) 2-butynyl]-2-pyrrolidinone

The title compound is prepared by the procedure of Example 10 up to and including the ozonization procedure with the substitution of the product from Example 6 for the product of Example 7.

CI-MS:m/z 237 (M+H+).

EXAMPLE 12

(S)-4-(1-Methylethyl)-3-(1-oxo-4-pentenyl)-2-oxazolidinone

To a −78° C. solution of 5.0 g of 4-(1-methylethyl)-2-oxazolidinone in 80 ml of tetrahydrofuran is added, dropwise, 15.5 ml of 2.5M n-butyl lithium in hexane. After stirring for 30 minutes, a solution of 4.8 g of 4-pentenyl chloride in 30 ml of tetrahydrofuran is added, dropwise, and the resulting solution is stirred at −78° C. for 3.5 hours. The reaction is diluted with aqueous ammonium chloride and diethyl ether. The organic layer is washed with water, dried and concentrated in vacuo. The residue is purified by chromatography (silica gel, 25% ethyl acetate/petroleum ether) to give 5.8 g of the desired product as a pale yellow oil.

$[\alpha]_D^{26°} = +79°$ (methylene chloride).

EXAMPLE 3

(4R-cis)-5-Methyl-3-(1-oxo-4-pentenyl)-4-phenyl-2-oxazolidinone

The title compound is prepared by the procedure of Example 12, using 8.0 g of (4R-cis)-5-methyl-3,4-phenyl-2-oxazolidinone, 18 ml of 2.5M n-butyl lithium and 5.0 g of 4-pentenyl chloride to give 10.3 g of the desired product as colorless crystals.

MP 69°–70° C.

$[\alpha]_D^{26°} = +34°$ (methylene chloride).

EXAMPLE 14

[S-(R*,R*)]-4-(1-Methylethyl)-3-(2-methyl-1-oxo-4-pentenyl)-2-oxazolidinone

To a −78° C. solution of 2.0 g of product from Example 12 in 40 ml of tetrahydrofuran is added, dropwise, 7.6 ml of 1.5M lithium diisopropylamide in tetrahydrofuran. The reaction is stirred at −78° C. for hour, 1.8 ml of iodomethane is added and the mixture stirred at −20° C. for 3 hours. The reaction is diluted with aqueous ammonium chloride and methylene chloride. The organic layer is washed with water, dried and concentrated in vacuo. The residue is purified by chromatography (silica gel, 25% ethyl acetate/hexane) to give 1.3 g of the product as colorless crystals.

MP 54°–55° C.

$[\alpha]_D^{26°} = +108°$ (methylene chloride).

EXAMPLE 15

[4R-[3(R*), 4 alpha,5 alpha]]-5-Methyl-3-(2-methyl-1-oxo-4-pentenyl)-4-phenyl-2-oxazolidinone The title compound is prepared by the procedure of Example 14, using 4.0 g of (4R-cis)-5-methyl-1-3-(-oxo-4-pentenyl)-4-phenyl-2-oxazolidinone, 12.3 ml of 1.5M lithium diisopropylamide and 1.8 ml of iodomethane to give 2.9 g of the desired product as a pale yellow oil.

$[\alpha]_D^{26°} = -2°$ (methylene chloride).

EXAMPLE 16

(S)-2-Methyl-4-pentenoic acid phenylmethyl ester

To a 0° C. solution of 5.1 g of benzyl alcohol in 50 ml of tetrahydrofuran is added, dropwise, 3.8 ml of 2.5M n-butyl lithium in hexane. To this mixture is added, via cannula, a solution of 3.5 g of S-(R*,R*)]4-(1-methylethyl)-3-(2-methyl-1-oxo-4-pentenyl)-2-oxazolidinone in 100 ml of tetrahydrofuran. The resulting solution is stirred at 0° C. for 2 hours. The reaction is diluted with saturated aqueous ammonium chloride and methylene chloride. The organic layer is washed with water, dried and concentrated in vacuo. The residue is purified by chromatography (silica gel, methylene chloride) to give 2.9 g of the desired product as a colorless oil.

$[\alpha]_D^{26°} = +3°$ (methylene chloride).

EXAMPLE 17

(R)-2-Methyl-4-pentenoic acid phenylmethyl ester

The title compound is prepared by the procedure of Example 16 using, 3.5 g of [4R-[3(R*),4 alpha, 5 alpha]]-5-methyl-3-(2-methyl-1-oxo-4-pentenyl)-4-phenyl-1-2-oxazolidinone, 4.2 g of benzyl alcohol and 3.1 ml of 2.5M n-butyl lithium to give 2.4 g of the desired product as a colorless oil.

$[\alpha]_D^{26°} = -2°$ (methylene chloride).

EXAMPLE 18

Racemic 2-methyl-4-pentenoic acid phenylmethyl ester

To 1.2L of ethyl alcohol under an atmosphere of argon is added, in portions, 14.9 g of sodium. After all the sodium is dissolved, 103 ml of diethyl methylmalonate is added and the reaction is stirred at room temperature for 30 minutes. Fifty-one ml of allyl bromide is added, dropwise, and the resulting solution is stirred at room temperature for 18 hours. The reaction is concentrated in vacuo and the residue partitioned between water and methylene chloride. The organic layer is dried and concentrated in vacuo to give 77.7 g of methyl 2-propenylpropane dicarboxylic acid diethyl ester.

A mixture of 77.7 g of methyl 2-propenylpropane dicarboxylic acid diethyl ester, 123 g of potassium hydroxide and 625 ml of ethyl alcohol is heated at reflux for 53 hours. The reaction is cooled, concentrated in vacuo and the residue partitioned between water and diethyl ether. The aqueous layer is separated, made acidic with concentrated hydrochloric acid, saturated with solid sodium chloride and extracted with diethyl ether. The combined diethyl ether layers are dried and concentrated in vacuo to give 80 g of methyl 2-propenylpropane dicarboxylic acid as colorless crystals; MP 89°–90° C.

Twenty three grams of methyl 2-propenylpropane dicarboxylic acid is heated in a Kugelrohr apparatus at 170° C. (20 mm/Hg). Sixteen grams of colorless liquid is collected in an ice cooled receiver. Distillation of the liquid gave racemic 2-methyl-4-pentenoic acid as a colorless liquid; bp 115°–125° C. at 20 mm Hg.

To a solution of 25 g of racemic 2-methyl-4-pentenoic acid, 0.3 g of dimethylformamide and 150 ml of methylene chloride is added, dropwise, 48.2 ml of oxalyl chloride. The resulting solution is stirred at room temperature until gas evolution ceases (3 hours). The reaction is concentrated in vacuo, diluted with methylene chloride and reconcentrated in vacuo to give 29.5 g of crude racemic 2-methyl-4-pentenoyl chloride.

To a 0° C. solution of 23.8 g of benzyl alcohol, 0.05 g of 4-(dimethylamino)pyridine, 18.3 g of pyridine and 250 ml of methylene chloride is added, dropwise, a solution of 29.5 g of racemic 2-methyl-4-pentenoyl chloride in 50 ml of methylene chloride. The mixture is stirred at room temperature for 4 hours, followed by successive washing with 2N hydrochloric acid, saturated sodium bicarbonate and saturated sodium chloride. The organic layer is dried and concentrated in vacuo. The residue is purified by Kugelrohr distillation to give 35.2 g of the desired product as a colorless oil; bp 70°–75° C. at 0.10 mm Hg.

EXAMPLE 19

Racemic 1-[4-(1-Dimethylamino)-2-butynyl]-3-methyl-2-pyrrolidinone

A stream of ozone is passed through a −78° C. solution of 1.0 g of racemic 2-methyl-4-pentenoic acid phenylmethyl ester in 110 ml of methyl alcohol until the blue color persists. The excess ozone is discharged by a stream of oxygen, followed by argon. One gram of zinc dust and 1.0 g of acetic acid is added and the resulting mixture allowed to warm to room temperature; followed by stirring for 1 hour. The excess zinc is removed by filtration and the filtrate is concentrated in vacuo. The residue is extracted with diethyl ether, filtered and the filtrate concentrated in vacuo. The residue is purified by pad filtration (silica gel, 50% diethyl ether/petroleum ether) to give 1.01 g of racemic 2-methyl-4-oxobutanoic acid phenylmethyl ester.

A solution of racemic 2-methyl-4-oxo-butanoic acid phenylmethyl ester in 5 ml of methyl alcohol is added to a room temperature solution of 3.0 g of N,N-dimethyl-2-butyne-1,4-diamine dihydrochloride, 2.5 g of sodium acetate and 30 ml of methyl alcohol. The resulting solution is stirred at room temperature for 15 minutes. One gram of sodium cyanoborohydride is added, in portions, over 2 hours and the resulting mixture is stirred for 18 hours. The reaction is made acidic with 1.0 ml of concentrated hydrochloric acid and concentrated in vacuo. The residue is made basic with sodium hydroxide and extracted with methylene chloride. The organic layer is washed with water, dried and concentrated in vacuo. The residue is purified by chromatography (alumina, activity grade 2.5, 25–100% ethyl acetate/petroleum ether) to give 5.7 g of the desired product as a pale yellow oil.

CI-MS:m/z 195 (M+H$^+$).

Following the general procedure of Example 19, the products of Examples 20–22, found in Table IV, are prepared.

TABLE IV

| Example | Starting Material # | Reactant | Product | $[\text{alpha}]_D^{26°}$ (methylene chloride) or CI-MS:m/z |
|---|---|---|---|---|
| 20 | 18 | 4 | Racemic 1-[4-(1-Diethylamino)-2-butynyl]-3-methyl-2-pyrrolidinone | 223 (M + H$^+$) |
| 21 | 16 | 3 | (S)-1-[4-(Dimethylamino)-2-butynyl]-3-methyl-2-pyrrolidinone | −21° |
| 22 | 17 | 3 | (R)-1-[4-(Dimethylamino)-2-butynyl]-3-methyl-2-pyrrolidinone | +22° |

EXAMPLE 23

(S)-1-(4-Bromo-2-buytynyl)-3-[[(1,1-dimethylethyl)-dimethylsilyl]oxy]-2-pyrrolidinone A mixture of 3.0 g of (S)-3-[[(1,1-dimethylethyl)dimethylsilyl]oxy]-1-propargyl-2-pyrrolidinone, 0.9 g of paraformaldehyde, 2.5 ml of diethylamine, 3.5 ml of acetic acid and 0.050 g of cuprous chloride is stirred at room temperature for 15 minutes, followed by heating at reflux temperature for 30 minutes. The reaction As cooled, concentrated in vacuo, made basic (pH 10) with ammonium hydroxide and partitioned between methylene chloride and water. The layers are separated, the aqueous layer reextracted and the methylene chloride extracts are combined. The organic solution is dried and concentrated in vacuo with 100 ml of toluene as co-solvent the residue is purified by chromatography (alumina, activity grade 2.5, 1–5% methyl alcohol/methylene chloride) to give 3.0 g of (S)-1-[4-(diethylamino)-2-butynyl]-3-[[(1,1-dimethylethyl)dimethylsily]oxy]-2-pyrrolidinone as a yellow oil.

$[\alpha]_D^{26°} = -56$ (methylene chloride).

A solution of 2.4 g of (S)-1-[4-diethylamino-2-butynyl]-3-[[(1,1-dimethylethyl)dimethylsilyl]oxy]-2-pyrrolidinone and 0.8 g of cyanogen bromide in 40 ml of diethyl ether is stirred at room temperature for 18 hours. The solution is washed with 30 ml of 1N hydrochloric acid and saturated sodium bicarbonate, dried and concentrated in vacuo. The residue is purified by chromatography (silica gel, methylene chloride) to give 2.0 g of the desired product as a colorless oil.

$[\alpha]_D^{26°} = -3$ (methylene chloride).

The starting (S)-3-[[(1,1-dimethylethyl)dimethylsilyl]oxy]-1-propargyl-2-pyrrolidinone is prepared by the procedure described in U.S. Pat. No. 4,937,235.

EXAMPLE 24

(R)-1-(4-Bromo-2-butynyl)-3-[[(1,1-dimethylethyl)-dimethylsilyl]]oxy]-2-pyrrolidinone The title compound is prepared by the procedure of Example 23 using 10.7 g of (R)-3-[[(1,1-dimethylethyl)-dimethylsilyl)oxy]-1-propargyl-2-pyrrolidinone, 8.7 ml of diethylamine, 3.2 g of paraformaldehyde, 0.10 g of cuprous chloride, 15 ml of acetic acid and 100 ml of dioxane. Ten grams of the diamine intermediate is treated with 3.5 g of cyanogen bromide in 150 ml of diethyl ether to give 2.05 g of the desired compound as a yellow oil.

$[\alpha]_D^{26°} = +26°$ (methylene chloride).

The starting (R)-3-[[(1,1-dimethylethyl)dimethylsilyl-]oxy]-1-propargyl-2-pyrrolidinone is prepared by the procedure described in U.S. Pat. No. 4,937,235.

EXAMPLE 25

1-(4-Bromo-2-butynyl-3-methyl)-2-pyrrolidine

To 31.0 g of N,N-diethyl-2-butyne-1,4-diamine dihydrochloride dissolved in 150 ml of methyl alcohol is added 30 ml of acetic acid and 23.8 g of sodium acetate. The resulting suspension is stirred as room temperature for 20 minutes. Ten grams of 2-methyl-4-oxo-butanoic acid phenylmethyl ester (intermediate in Example 19), is added and the mixture is stirred for 15 minutes. Three grams of sodium cyanoborohydride is added in portions and the mixture is stirred at room temperature for 18 hours.

The reaction mixture is concentrated in vacuo, made basic (pH 12) with 5N sodium hydroxide and extracted with methylene chloride. The combined organic layers are dried, filtered and concentrated in vacuo to give 9.7 g of oil. The oil is purified by chromatography (alumina, activity grade 2.5, 0–75% ethyl acetate/petroleum ether) to give 5.9 g of 1-[4-(diethylamino)-2-butynyl]-3-methyl-2-pyrrolidinone.

CI-MS:m/z 223 (M±H).

A solution of 2.7 g of cyanogen bromide in 50 ml of diethyl ether is added to 5.1 g of 1-[4-(diethylamino)-2-butynyl]-3-methyl-2-pyrrolidinone dissolved in 50 ml diethyl ether. The reaction is stirred at room temperature for 66 hours. The mixture is washed with 1N hydrochloric acid and saturated sodium bicarbonate, dried, filtered and concentrated in vacuo to give 7.1 g of a light yellow oil. The oil is purified by chromatography (silica gel, petroleum ether/ethyl acetate) to give 3.8 g of the desired product.

CI-MS:m/z 247 (M+NH$_4$+).

EXAMPLE 26

(S)-3-[[(1,1-Dimethylethyl)dimethylsilyl]oxy]-1-[4-(1H-imidazol-1-yl)-2-butynyl]-2-pyrrolidinone A solution of 2.0 g of (S)-1-(4-bromo-2-butynyl)-3-[[(1,1-dimethylethyl)dimethylsilyl]oxy]-2-pyrrolidinone, 1–3 g of imidazole and 50 ml of tetrahydrofuran is stirred at room temperature for 72 hours. The solution is concentrated in vacuo. The residue is purified by chromatography (alumina, activity grade 2.5, 2% methyl alcohol/methylene chloride) to give 1.6 g of the desired product as a colorless oil.

$[\alpha]_D^{26°} = -30°$ (methylene chloride).

EXAMPLE 21

(S)-3-Hydroxy-1-[4(1H-imidazol-1-yl)-2-butynyl]2-pyrrolidinone

A solution of 1.6 g of 1-(4-bromo-2-butynyl)-3-[[(1,1-dimethylethyl)dimethylsilyl]oxy]-2-pyrrolidinone in 15 ml of 1N methanolic hydrogen chloride is stirred at room temperature for 2 hours. The reaction is concentrated in vacuo, partitioned between methylene chloride and saturated sodium carbonate and the layers are separated. The organic layer is dried and concentrated in vacuo. The residue is purified by chromatography (alumina, activity grade 2.5, 2% methyl alcohol/methylene chloride) to give 0.9 g of the desired product as off-white crystals.

MP 127°–128° C.

$[\alpha]_D^{26°} = -47°$. (methylene chloride).

Following the general procedure of Examples 26 and 27, the products of Examples 28–33 found in Table V are prepared.

TABLE V

| Example | Starting Material # | Reactant | Product | $[alpha]_D^{26°}$ (methylene chloride) |
|---|---|---|---|---|
| 28 | 23 | Azetidine | (S)-1-[4-(1-Azetidinyl)--2-butynyl]-3-[[(1,1-dimethylethyl)-dimethylsilyl]oxy]-2-pyrrolidinone | −34° |
| 29 | 24 | Imidazole | (R)-3-([[(1,1-Dimethylethyl)-dimethylsilyl]oxy]-1-[4-(1H-imidazol-1-yl)-2-butynyl]-2-pyrrolidinone | +32° |
| 30 | 24 | Azetidine | (R)-1-[4-(1-Azetidinyl)-2-butynyl]-3-[[(1,1-dimethylethyl)dimethylsilyl]oxy]-2-pyrrolidinone | +36° |
| 31 | 28 | Methanolic hydrogen chloride | (S)-3-Hydroxy-1-[4-(1-azetidinyl)-2-butynyl]-2-pyrrolidinone | (not stable) |
| 32 | 29 | Methanolic hydrogen chloride | 1-[4-(1H-Imidazol-1-yl)-2-butynyl]-3-hydroxy-2-pyrrolidinone | +39° |
| 33 | 30 | Methanolic hydrogen chloride | (R)-3-Hydroxy-1-[4-(1-azetidinyl)-2-butynyl]-2-pyrrolidinone | (not stable) |

Examples 34–49 (Table VI) are prepared according to the procedures described in U.S. Pat. No. 4,937,235. An alternate synthetic pathway to the products in Examples 34–49 can be achieved using the process described in Examples 23 and 24.

TABLE VI

| Example | Starting Material # | Reactant | Product | [alpha]$_D^{26°}$ or CI-MS: m/z |
|---|---|---|---|---|
| 34 | 23 | Dimethylamine | (S)-1-[4-(Dimethylamino)-2-butynyl]-3-[[(1,1-dimethylethyl)dimethylsilyl]oxy]-2-pyrrolidinone | −37° (mc) |
| 35 | 24 | Dimethylamine | (R)-1-[4-(Dimethylamino)-2-butynyl]-3-[[(1,1-dimethylethyl)dimethylsilyl]oxy]-2-pyrrolidinone | ND |
| 36 | 34 | Methanolic hydrogen chloride | (S)-1-[4-(Dimethylamino)-2-butynyl]-3-hydroxy-2-pyrrolidinone | −71° (mc) |
| 37 | 35 | Methanolic hydrogen chloride | (R)-1-[4-(Dimethylamino)-2-butynyl-3-hydroxy-2-pyrrolidinone | +69° (mc) |
| 38 | 23 | Pyrrolidine | (S)-3-[[(1,1-Dimethylethyl)dimethylsilyl]oxy]-1-[4-(1-pyrrolidinyl)-2-butynyl]-2-pyrrolidinone | −35° (mc) |
| 39 | 24 | Pyrrolidine | (R)-3-[[(1,1-Dimethylethyl)dimethylsilyl]oxy]-1-[4-(1-pyrrolidinyl)-2-butynyl]-2-pyrrolidinone | ND |
| 40 | 23 | Methanolic hydrogen chloride | (S)-3-Hydroxy-1-[4-(1-pyrrolidinyl)-2-butynyl]-2-pyrrolidinone | −63° (ma) |
| 41 | 24 | Methanolic hydrogen chloride | (R)-3-Hydroxy-1-[4-(1-pyrrolidinyl)-2-butynyl]-2-pyrrolidinone | +60° (ma) |
| 42 | 23 | Methylaminoethanol | (S)-3-[[(1,1-Dimethylethyl)dimethylsilyl]oxy]-1-[4-[(2-hydroxyethyl)methylamino]-2-butynyl]-2-pyrrolidinone | ND (intermediate) |
| 43 | 42 | Methanolic hydrogen chloride | (S)-3-Hydroxy-1-[4-[(2-hydroxyethyl)methylamino]-2-butynyl]-2-pyrrolidinone | −38° (ma) |
| 44 | 24 | Methylaminobutanol | (S)-3-([[(1,1-Dimethylethyl)dimethylsilyl]oxy]-1-[4-[(4-hydroxybutyl)methylamino]-2-butynyl]-2-pyrrolidinone- | ND (intermediate) |
| 45 | 44 | Methanolic hydrogen chloride | (R)-3-Hydroxy-1-[4-[(4-hydroxybutyl)methylamino]-2-butynyl]-2-pyrrolidinone | +33° (ma) |
| 46 | 25 | Imidazole | Racemic 1-[4-(1H-imidazol-1-yl)-2-butynyl]-3-methyl-2-pyrrolidinone | 218 (M + H$^+$) |
| 47 | 25 | Azetidine | Racemic 1-[4-(1-azetidinyl)-2-butynyl]-3-methyl-2-pyrrolidinone | 207 (M + H$^+$) |
| 48 | 25 | (S)-3[[(1,1-Dimethylethyl)dimethylsilyl]oxy]methyl]-1-pyrrolidinone | [R-[(R*, R* and R*, S*)]]-1-[4-[2-[[[(1,1-dimethylethyl)dimethylsilyl]oxy]methyl]-1-pyrrolidinyl]-2-butynyl]-3-methyl-2-pyrrolidinone | 365 (M + H$^+$) |
| 49 | 25 | (S)-3-[[(1,1-dimethylethyl)dimethylsilyl]-1-pyrrolidine carboxylic acid phenyl methyl ester | [R-(R*, R* and R*, S*)]-1-[4-(3[[(1,1-dimethylethyl)dimethylsilyl]oxy]-1-pyrrolidinyl-2-butynyl]-3-methyl-2-pyrrolidinone | −2° (mc) 351 (M + H$^+$) |

ND = Not done
(mc) = Rotation done in methylene chloride
(ma) = Rotation done in methyl alcohol

EXAMPLE 50

(S)-2-[[[(1,1-Dimethylethyl)dimethylsilyl]oxy]methyl]-1-pyrrolidinecarboxylic acid phenylmethyl ester To a 0° C. solution of 25 g of (S)-2-pyrrolidinemethanol in 150 ml of diethyl ether is added 54.8 g of benzyl chloroformate. At mid point of addition, 49.4 ml of 5N sodium hydroxide is added, simultaneously, and the reaction stirred at 0° C. for 2 hours. Diethyl ether is added, the layers are separated and the aqueous layer reextracted with diethyl ether. The combined organic layers are dried, filtered and concentrated in vacuo. The residue is purified by chromatography (silica gel, 0–10% methyl alcohol/methylene chloride) to give 59.1 g of (S)-2-hydroxymethyl-1-pyrrolidine carboxylic acid phenylmethyl ester.

A solution 58.0 g of (S)-2-hydroxymethyl-1-pyrrolidine carboxylic acid phenylmethyl ester, 45.0 g of (1,1-dimethylethyl)dimethylsilylchloride, 69 ml of triethylamine, 1.50 g of 4-(dimethylamino)pyridine and 50 ml of methylene chloride is stirred at room temperature for 18 hours. The resulting solution is washed with water, 2N hydrochloric acid, saturated sodium bicarbonate and sodium chloride. The organic layer is dried and concentrated in vacuo. The residue, dissolved in methylene chloride, is filtered through a silica gel pad and concentrated in vacuo to give 76.5 g of the desired product as a colorless oil.

$[\alpha]_D^{26°} = -46°$ (methylene chloride).

EXAMPLE 51

(R)-2-[[[(1,1-Dimethylethyl]dimethylsilyl]oxy]methyl]-1-pyrrolidinecaboxylic acid phenylmethyl ester The title compound is prepared by the procedure of Example 50 using 20.0 g of (R)-2-pyrrolidinemethanol, 44.0 g of benzyl chloroformate and 200 ml of diethyl ether to give 56.4 g of (R)-2-hydroxymethyl-1-pyrrolidine carboxylic acid phenyl methyl ester. Forty-five g of (R)-2-hydroxymethyl-1-pyrrolidine carboxylic acid phenylmethyl ester is reacted with 38.4 g of (1,1-dimethylethyl)dimethylsilylchloride, 58 ml of triethylamine, 1.3 g of 4-(dimethylamino)pyridine and 450 ml of methylene chloride to give 41.5 g of the desired product as a colorless oil.

$[\alpha]_D^{26°} = +45°$ (methylene chloride).

EXAMPLE 52

(S)-3-(Acetoxy)-1-(2-propynyl]-2-pyrrolidinone

A solution of 4.3 g of (S)-3-hydroxy-1-(2-propynyl)-2-pyrrolidinone, 10.6 ml of acetic anhydride, 0.6 ml of pyridine, 0.1 g of 4-(dimethylamino)pyridine and 85 ml of methylene chloride is stirred at room temperature for 18 hours. Twenty-five ml of methyl alcohol is added and the reaction stirred for 20 minutes. The mixture is washed with 1N hydrochloric acid and saturated sodium bicarbonate. The organic layer is dried, passed thorough a pad of hydrous magnesium silicate and concentrated in vacuo to give 4.9 g of the desired product as a pale yellow oil.

$[\alpha]_D^{26°} = +60°$ (methylene chloride).

EXAMPLE 53

(R)-3-(Acetoxy)-1-(2-propynyl)-2-pyrrolidinone

The title compound is prepared by the procedure of Example 52 using 19.6 g of (R)-3-hydroxy-1-(2-propynyl)-2-pyrrolidinone, 26.6 ml of acetic anhydride, 17 ml of pyridine, 0.6 g of 4-(dimethylamino)pyridine and 200 ml of methylene chloride to give 23.4 g of the desired product as a pale yellow oil.

$[\alpha]_D^{26°} = +59°$ (methylene chloride).

EXAMPLE 54

(R*,S*)]-3-(Acetoxy)-1-[4-[2-[[[(1,1-dimethylethyl)-dimethylsilyl]oxy]methyl]-1-pyrrolidinyl]-2-butynyl]-2-pyrrolidinone A mixture of 7.3 g of (S)-3[[(1,1-dimethylethyl)dimethylsilyl]oxy]methyl]-1-pyrrolidine carboxylic acid phenylmethyl ester, 0.40 g of 10% palladium on carbon and 225 ml of ethyl alcohol is hydrogenated in a Parr apparatus at room temperature under atmospheric pressure. The catalyst is removed by filtration, the filtrate is diluted with 100 ml of toluene and concentrated in vacuo. The residue is treated with 2.4 g of product from Example 53, 0.65 g of paraformaldehyde, 0.38 g of cuprous chloride, 1.8 ml of acetic acid and 75 ml of dioxane. The resulting mixture is heated at reflux temperature for 45 minutes, cooled, made basic with ammonium hydroxide and extracted with methylene chloride. The organic layer is washed with water, dried and concentrated in vacuo. The residue is purified by chromatography (alumina, activity grade 2.5, 1% methyl alcohol/methylene chloride) to give 3.6 g of the desired product as an orange/red oil.

$[\alpha]_D^{26°} = -4°$ (methyl alcohol).

Following the general procedure for Example 54, the products of Examples 55–61, found in Table VII, are prepared.

TABLE VII

| Example | Starting Material # | Reactant | Product | $[alpha]_D^{26°}$ (methyl alcohol) |
|---|---|---|---|---|
| 55 | 52 | 50 | [S-(R*, R*)]-3-(Acetyloxy)-1-[4-[2-[[[(1,1-dimethylethyl)-dimethylsilyl]oxy]methyl]-1-pyrrolidinyl]-2-butynyl]-2-pyrrolidinone | −56° |
| 56 | 52 | 51 | [S-(R*, S*)]-3-(Acetyloxy)-1-[4-[2-[[[(1,1-dimethylethyl)dimethylsilyl]oxy]methyl]-1-pyrrolidinyl]-2-butynyl]-2-pyrrolidinone | −4° |
| 57 | 53 | 51 | [R-(R*, R*)]-3-Acetyloxy)-1-[4-[2-[[[(1,1-dimethylethyl)-dimethylsilyl]oxy]methyl]-1-pyrrolidinyl]-2-butynyl]-2-pyrrolidinone | +53° |
| 58 | 52 | 2-(Methylamino)ethanol | (S)-3-(Acetyloxy)-1-[4-[2-(hydroxyethyl)methylamino]-2-butynyl]-2-pyrrolidinone | −45° |
| 59 | 53 | 2-(Methylamino)ethanol | (R)-3-(Acetyloxy)-1-[4-[2-(hydroxyethyl)methylamino]-2-butynyl]-2-pyrrolidinone | +45° |
| 60 | 52 | 2-(Methylamino)butanol | (S)-3-(Acetyloxy)-1-[4-[(4-hydroxybutyl)methylamino]-2-butynyl]-2-pyrrolidinone | −43° |
| 61 | 53 | 2-(Methylamino)butanol | (R)-3-(Acetyloxy)-1-[4-[(4-hydroxybutyl)methylamino]-2-butynyl]-2- | +43° |

EXAMPLE 62

[R-(R*,S*)]-1-[4-[2-[[[(1,1-dimethylethyl)dimethylsilyl]oxy]methyl]-1-pyrrolidinyl]-2-butynyl]-3-hydroxy-2-pyrrolidone A solution of 0.90 g of product from Example 54, 1.4 g of potassium carbonate and 25 ml of methyl alcohol is stirred at room temperature for 4 hours. The solution is passed through a pad of diatomaceous earth and the filtrate concentrated in vacuo. The residue is purified by chromatography (alumina, activity grade 2.5, 10% methyl alcohol/methylene chloride) to give 0.42 g of the desired product as a red/orange oil.

$[\alpha]_D^{26°} = -15°$ (methyl alcohol).

Following the general procedure of Example 62, the products of Examples 63–69, found in Table VIII, are prepared.

EXAMPLE 70

[S-(R*,S*)]-3-Hydroxy-1-[4-[2-(hydroxymethyl)-1-pyrrolidinyl]-2-butynyl]-2-pyrrolidinone A solution of 1.62 g of product from Example 64, 35 ml of methyl alcohol and 2.1 ml of concentrated hydrochloric acid is stirred at room temperature for 4 hours. The solution is concentrated in vacuo and the residue is partitioned between 10N sodium hydroxide and methylene chloride. The organic layer is dried and concentrated in vacuo. The residue is purified by pad filtration (alumina, 10% methyl alcohol/methylene chloride) to give 0.910 g of the desired product as a viscous yellow oil.

$[\alpha]_D^{26°} = +2°$ (methyl alcohol).

Following the general procedure of Example 70, the products of Examples 71 & 72, found in Table IX, are prepared.

TABLE VII-continued

| Example | Starting Material # | Reactant | Product | $[alpha]_D^{26°}$ (methyl alcohol) |
|---|---|---|---|---|
| | | | pyrrolidinone | |

TABLE VIII

| Example | Starting Material # | Reactant | Product | $[alpha]_D^{26°}$ (methyl alcohol) |
|---|---|---|---|---|
| 63 | 55 | Potassium carbonate | [S-(R*, R*)]-1-[4-[2-[[[(1,1-Dimethylethyl)dimethylsilyl]oxy]methyl]-1-pyrrolidinyl]-2-butynyl]-3-hydroxy-2-pyrrolidinone | −59° |
| 64 | 56 | Potassium carbonate | [S-(R*, S*)]-1-(4-[2-[[[(1,1-Dimethylethyl)dimethylsilyl]oxy]methyl]-1-pyrrolidinyl]-2-butynyl]-3-hydroxy-2-pyrrolidinone | +7° |
| 65 | 57 | Potassium carbonate | [R-(R*, R*)]-1-[4-[2-[[[(1,1-Dimethylethyl)dimethylsilyl]oxy]methyl]-1-pyrrolidinyl]-2-butynyl]-3-hydroxy-2-pyrrolidinone | +46° |
| 66[a] | 58 | Potassium carbonate | (S)-3-Hydroxy-1-[4-[(2-hydroxyethyl)methylamino]-2-butynyl]-2-pyrrolidinone | −38° |
| 67 | 59 | Potassium carbonate | (R)-3-Hydroxy-1-[4-[(2-hydroxyethyl)methylamino]-2-butynyl]-2-pyrrolidinone | +36° |
| 68 | 60 | Potassium carbonate | (S)-3-Hydroxy-1-[4-[(4-hydroxybutyl)methylamino]-2-butynyl]-2-pyrrolidinone | −35° |
| 69[b] | 61 | Potassium carbonate | (R)-3-Hydroxy-1-[4-[(4-hydroxybutyl)methylamino]-2-butynyl]-2-pyrrolidinone | +33° |

[a]Same product as Example 43.
[b]Same product as Example 45.

TABLE IX

| Example | Starting Material # | Reactant | Product | $[alpha]_D^{26°}$ (methyl alcohol) |
|---|---|---|---|---|
| 71 | 63 | Hydrochloric acid | [S-(R*, R*)]-3-Hydroxy-1-[4-[2-(hydroxymethyl)-1-pyrrolidinyl]-2-butynyl]-2-pyrrolidinone | −73° (methyl alcohol) |
| 72 | 62 | Hydrochloric acid | [R-(R*, S*)]-3-Hydroxy-1-[4-[2-(hydroxymethyl)-1-pyrrolidinyl]-2-butynyl]-2-pyrrolidinone | ND |

ND = Not done

EXAMPLE 73

(S)-3-(Methylthio)-1-[4-(1-pyrrolidinyl)-2-butynyl]-2-pyrrolidinone

A solution of 1.2 g of (S)-3-thio-1-[4-(1-pyrrolidinyl)-2-butynyl]-2-pyrrolidinone in 100 ml of methylene chloride is added to a stirred suspension of 31 g of activated silica gel in 100 ml of methylene chloride. The mixture is stirred for 15 minutes to ensure absorption of the thiol on the silica gel. Two hundred and twenty ml of 0.4M diethyl ether solution of diazomethane is added in portions over 30 minutes. The solution is filtered and the silica gel washed thoroughly with methyl alcohol. The filtrate is concentrated in vacuo and the residue purified by chromatography (alumina, activity grade 2.5, 1% methyl alcohol/methylene chloride) to give 0.275 g of the desired product as a red/orange oil.

$[\alpha]_D^{26°} = -49°$ (methyl alcohol).

Following the general procedure of Example 73, the products of Examples 74–77, found in Table X, are prepared.

centrated in vacuo. The resulting 1.2 g of the methanesulfonate is used without further purification.

A solution of 1.2 g of the methanesulfonate, 1.4 g of sodium azide and 25 ml of methyl alcohol is stirred at room temperature for 18 hours; followed by heating at reflux temperature for 1.5 hours. The reaction is cooled, diluted with diethyl ether and filtered through a pad of diatomaceous earth. The filtrate is concentrated in vacuo and the residue partitioned between water and methylene chloride. The organic layer is dried, concentrated in vacuo, and the residue is purified by chromatography (alumina, activity grade 2.5, 1% methyl alcohol/methylene chloride) to give 0.88 g of the desired product as a pale yellow oil.

$[\alpha]_D^{26°} = -175°$

EXAMPLE 79

(S)-3-Amino-1-[4-(1-pyrrolidinyl)-2-butynyl]-2-pyrrolidinone dihydrochloride

A mixture of 0.70 g of product from Example 78, 9.5 g of zinc dust and 10 ml of acetic acid is stirred at room

TABLE X

| Example | Starting Material # | Reactant | Product | $[alpha]_D^{26°}$ (methyl alcohol) |
|---|---|---|---|---|
| 74 | (R)-3-Thio-1-[4-(1-pyrrolidinyl)-2-butynyl-2-pyrrolidinone | Diazomethane | (R)-3-(Methylthio)-1-[4-(1-pyrrolidinyl)-2-butynyl]-2-pyrrolidinone | +40° |
| 75 | (S)-3-Thio-1-[4-(1-dimethylamino)-2-butynyl]-2-pyrrolidinone | Diazomethane | (S)-1-[4-(Dimethylamino)-2-butynyl]-3-(methylthio)-2-pyrrolidinone | −53° |
| 76 | (R)-3-Thio-1-[4-(1-dimethylamino)-2-butynyl]-2-pyrrolidinone | Diazomethane | (R)-1-[4-(Dimethylamino)-2-butynyl]-3-(methylthio)-2-pyrrolidinone | +45° |
| 77 | 75 | Methyl iodide | (S)-N,N,N-Trimethyl-4-[3-(methylthio)-2-oxo-1-pyrrolidinyl]-2-butyn-1-aminium iodide | +31° |

EXAMPLE 78

(S)-3-Azido-1-[4-(1-pyrrolidinyl)-2-butynyl]-2-pyrrolidinone

A solution of 0.75 ml of methanesulfonyl chloride in 5 ml of methylene chloride is added, dropwise, to a 0° C. solution of 1.0 g of product from Example 46, 1.5 ml of triethylamine and 25 ml of methylene chloride. The mixture is stirred at 0° C. for 1½ hours. The reaction is diluted with methylene chloride and saturated sodium carbonate. The organic layer is washed with saturated sodium chloride, dried, diluted with toluene and contemperature for 1.5 hours. The reaction is filtered, the zinc is washed with methylene chloride and the filtrate concentrated in vacuo. The residue is partitioned between methylene chloride and 6 ml of ammonium hydroxide. The organic layer is dried and concentrated in vacuo. The residue is dissolved in 1N methanolic hydrogen chloride and diluted with diethyl ether. The resulting precipitate is collected and recrystallized from ethyl alcohol/diethyl ether to give 0.24 g of the desired product as colorless crystals.

MP 224°–226° C.

$[\alpha]_D^{26°} = -29°$ (methyl alcohol).

Following the general procedure of Example 79, the products of Examples 80–87, found in Table XI, are prepared.

TABLE XI

| Example | Starting Material # | Reactant | Product | MP °C. or $[alpha]_D^{26°}$ (methyl alcohol) |
|---|---|---|---|---|
| 80 | (R)-3-Hydroxy-1-[4-(1-pyrrolidinyl)-2-butynyl]-2-pyrrolidinone | Sodium azide | (R)-3-Azido-1-[4-(1-pyrrolidinyl)-2-butynyl]-2-pyrrolidinone | +190° |
| 81 | (S)-3-Hydroxy-1-[4-(1-dimethylamino)-2-butynyl]-2-pyrrolidinone | Sodium azide | (S)-3-Azido-1-[4-(dimethylamino)-2-butynyl]-2-pyrrolidinone | −188° |
| 82 | (R)-3-Hydroxy-1- | Sodium | (R)-3-Azido-1-[4- | +185° |

TABLE XI-continued

| Example | Starting Material # | Reactant | Product | MP °C. or [alpha]$_D^{26°}$ (methyl alcohol) |
|---|---|---|---|---|
| | | azide | [4-(1-dimethyl-amino)-2-butynyl]-2-pyrrolidinone | |
| | | | (dimethylamino)-2-butynyl]-2-pyrrolidinone | |
| 83 | 81 | Methyl iodide | (S)-4-(3-Azido-2-oxo-1-pyrrolidinyl)-N,N,N-trimethyl-2-butyn-1-aminium iodide | −122° |
| 84 | 82 | Methyl iodide | (R)-4-(3-Azido-2-oxo-1-pyrrolidinyl)-N,N,N-trimethyl-2-butyn-1-aminium iodide | +103° |
| 85 | 80 | Zinc/acetic acid | (R)-3-Amino-1-[4-(1-pyrrolidinyl)-2-butynyl]-2-pyrrolidinone dihydrochloride | −30° |
| 86 | 81 | Zinc/acetic acid | (S)-3-Amino-1-[4-(dimethylamino)-2-butynyl]-2-pyrrolidinone dihydrochloride | −33° |
| 87 | 82 | Zinc/acetic acid | (R)-3-Amino-1-(4-(dimethylamino)-2-butynyl]-2-pyrrolidinone dihydrochloride | +32° |

EXAMPLE 88

(S)-2-Methylpropanoic acid 1-[4-(dimethylamine)-2-butynyl]-2-oxo-3-pyrrolidinyl ester A solution of 0.84 g of isobutyryl chloride in 15 ml of methylene chloride is added, dropwise, to a 0° C. solution of 1.4 g of (S)-3-hydroxy-1-[4-(1-dimethylamino)-2-butynyl]-2-pyrrolidinone, 3 ml of triethylamine, 0.10 g of 4-(dimethylamino)pyridine and 25 ml methylene chloride. The mixture is stirred at room temperature for 18 hours. Two ml of methyl alcohol is added and the methylene chloride solution is washed with 1N hydrochloric acid and saturated sodium carbonate, dried and concentrated in vacuo. The residue is purified by chromatography (alumina, activity grade 2.5, 1% methyl alcohol/methylene chloride) to give 1.65 g of the desired product as a pale yellow oil.

$[\alpha]_D^{26°} = -44°$ (methylene chloride).

Following the general procedure of Example 88, the products of Examples 89–124, found in Table XII, are prepared.

TABLE XII

| Example | Starting Material # | Reactant | Product | MP °C. or [alpha]$_D^{26°}$ (methyl alcohol) |
|---|---|---|---|---|
| 89 | 37 | 2,2-Dimethylpropanoyl chloride | (S)-2,2-Dimethylpropanoic acid 1-[4-(dimethylamino)-2-butynyl]-2-oxo-3-pyrrolidinyl ester | −39° |
| 90 | 37 | Decanoyl chloride | (S)-Decanoic acid 1-[4-(dimethylamino)-2-butynyl]-2-oxo-3-pyrrolidinyl ester | −36° |
| 91 | 37 | Octyl chloroformate | (S)-Carbonic acid 1-[4-(dimethylamino)-2-butynyl]-2-oxo-3-pyrrolidinyl octyl ester | −40° |
| 92 | 37 | Methyl chloroformate | (S)-Carbonic acid 1-[4-(dimethylamino)-2-butynyl]-2-oxo-3-pyrrolidinyl methyl ester | −60° |
| 93 | 90 | Methyl iodide | (S)-N,N,N-Trimethyl-4-[2-oxo-3-[(1-oxodecyl)oxy]-1-pyrrolidinyl-2-butyn-1-aminium iodide | −28° |
| 94 | 88 | Methyl iodide | (S)-N,N,N-Trimethyl-4-[3-(2-methyl-1-oxopropoxy)-2-oxo-1-pyrrolidinyl]-2-butyn-1-aminium iodide | −35° |
| 95 | 89 | Methyl iodide | (S)-4-[3-(2,2-Dimethyl-1-oxopropoxy)-2-oxo-1-pyrrolidinyl]-N,N,N-trimethyl-2-butyn-1-aminium iodide | −33° |
| 96 | 91 | Methyl iodide | (S)-N,N,N-Trimethyl-4-[3-[[(oxtyloxy)carbonyl]oxy]-2-oxo-1-pyrrolidinyl]-2-butyn-1-aminium iodide | −33° |
| 97 | 40 | Isobutyryl chloride | (S)-2-Methylpropanoic acid 2-oxo-1-[4-(1-pyrrolidinyl)-2-butynyl]-3-pyrrolidinyl | −42° |

TABLE XII-continued

| Example | Starting Material # | Reactant | Product | MP °C. or [alpha]$_D^{26°}$ (methyl alcohol) |
|---|---|---|---|---|
| | | | ester | |
| 98 | 40 | Pivaloyl chloride | (S)-2,2-Dimethylpropanoic acid 2-oxo-1-[4-(1-pyrrolidinyl)-2-butynyl]-3-pyrrolidinyl ester | −37° |
| 99 | 40 | Methyl isocyanate | (S)-3-[[Methylamino)carbonyl]oxy]-1-[4-(1-pyrrolidinyl)-2-butynyl]-2-pyrrolidinone | −39° |
| 100 | 40 | Dimethylcarbamoyl chloride | (S)-Dimethylcarbamic acid 2-oxo-1-[4-(1-pyrrolidinyl)-2-butynyl]-3-pyrrolidinyl ester | −33° |
| 101 | 40 | Hexyl chloroformate | (S)-Carbonic acid hexyl 2-oxo-1-[4-(1-pyrrolidinyl)-2-butynyl]-3-pyrrolidinyl ester | −43° |
| 102 | 40 | t-Butyl chloroformate | (S)-Carbonic acid 1,1-dimethylethyl-2-oxo-1-[4-(1-pyrrolidinyl)-2-butynyl]-3-pyrrolidinyl ester | −46° |
| 103 | 40 | Methyl chloroformate | (S)-Carbonic acid methyl 2-oxo-1-[4-(1-pyrrolidinyl)-2-butynyl]-3-pyrrolidinyl ester | −56° |
| 104 | 36 | Isobutyryl chloride | (R)-Propanoic acid 2-methyl-1-[4-(dimethylamino)-2-butynyl]-2-oxo-3-pyrrolidinyl ester | +44° |
| 105 | 36 | Pivaloyl chloride | (R)-2,2-Dimethylpropanoic acid 1-[4-(dimethylamino)-2-butynyl]-2-oxo-3-pyrrolidinyl ester | +38° |
| 106 | 36 | Decanoyl chloride | (R)-Decanoic acid 1-[4-(dimethylamino)-2-butynyl]-2-oxo-3-pyrrolidinyl ester | +35° |
| 107 | 36 | Decanoyl chloride | (R)-Octylcarbamic acid 1-[4-(dimethylamino)-2-butynyl]-2-oxo-3-pyrrolidinyl ester | +28° |
| 108 | 36 | Methyl chloroformate | (R)-Carbonic acid 1-[4-(dimethylamino)-2-butynyl]-2-oxo-3-pyrrolidinyl methyl ester monohydrochloride | +61° |
| 109 | 36 | Octyl chloroformate | (R)-Carbonic acid 1-[4-(dimethylamino)-2-butynyl]-2-oxo-3-pyrrolidinyl octyl ester | +36° |
| 110 | 104 | Methyl iodide | (R)-N,N,N-Trimethyl-4-[3-(2-methyl-1-oxopropoxy)-2-oxo-1-pyrrolidinyl]-2-butyn-1-aminium iodide | +35° MP 128–130° |
| 111 | 105 | Methyl iodide | (R)-4-[3-(2,2-Dimethyl-1-oxopropoxy)-2-oxy-1-pyrrolidinyl]-N,N,N-trimethyl-2-butyn-1-aminium iodide | +32° MP 160–162° |
| 112 | 106 | Methyl iodide | (R)-4-[2-Oxo-3-[(1-oxodecyl)oxy]-1-pyrrolidinyl]-N,N,N-trimethyl-2-butyn-1-aminium iodide | +28° MP 103–105° |
| 113 | 107 | Methyl iodide | (R)-N,N,N-Trimethyl-4-[3-[[(octylamino)carbonyl]oxy]-2-oxo-1-pyrrolidinyl]-2-butyn-1-aminium iodide | +34° |
| 114 | 109 | Methyl iodide | (R)-N,N,N-Trimethyl-4-[3-[[(octyloxy)carbonyl]oxy]-2-oxo-1-pyrrolidinyl]-2-butyn-1-aminium iodide | +34° |
| 115 | 41 | Isobutyryl chloride | (R)-2-Methylpropanoic acid 2-oxo-1-[4-(1-pyrrolidinyl)-2-butynyl]-3-pyrrolidinyl ester | +42° |
| 116 | 41 | Pivaloyl chloride | (R)-2,2-Dimethylpropanoic acid 2-oxo-1-[4-(1-pyrrolidinyl)-2-butynyl]-3-pyrrolidinyl ester | +37° |
| 117 | 41 | Decanoyl chloride | (R)-Decanoic acid 2-oxo-1-[4-(1-pyrrolidinyl)-2-butynyl]-3-pyrrolidinyl ester | +35° |
| 118 | 41 | Benzyl chloroformate | (R)-Carbonic acid 2-oxo-1-[4-(1-pyrrolidinyl)-2-butynyl]-3-pyrrolidinyl | +38° |

TABLE XII-continued

| Example | Starting Material # | Reactant | Product | MP °C. or [alpha]$_D^{26°}$ (methyl alcohol) |
|---|---|---|---|---|
| 119 | 41 | Octyl isocyanate | phenylmethyl ester (R)-Octylcarbamic acid 2-oxo-1-[4-(1-pyrrolidinyl)-2-butynyl]-3-pyrrolidinyl ester | +28° MP 47-49° |
| 120 | 41 | Octyl chloroformate | (R)-Carbonic acid octyl 2-oxo-1-[4-(1-pyrrolidinyl)-2-butynyl]-3-pyrrolidinyl ester | +39° |
| 121 | 41 | Methyl chloroformate | (R)-Carbonic acid methyl 2-oxo-1-[4-(1-pyrrolidinyl)-2-butynyl]-3-pyrrolidinyl ester | +56° |
| 122 | (S)-4-Hydroxy-1-[4-(1-pyrrolidinyl)-2-butynyl]-2-pyrrolidinone | Decanoyl chloride | (S)-Decanoic acid 2-oxo-1-[4-(1-pyrrolidinyl)-2-butynyl]-4-pyrrolidinyl ester | -36° |
| 123 | (S)-4-Hydroxy-1-[4-(1-pyrrolidinyl)-2-butynyl]-2-pyrrolidinone | Methyl chloroformate | (S)-Carbonic acid methyl 2-oxo-1-[4-(1-pyrrolidinyl)-2-butynyl]-4-pyrrolidinyl ester | -5° |
| 124 | (S)-4-Hydroxy-1-[4-(1-pyrrolidinyl)-2-butynyl-2-pyrrolidinone | Octyl isocyanate | (S)-Octylcarbamic acid 2-oxo-1-[4-(1-pyrrolidinyl)-2-butynyl]-4-pyrrolidinyl ester | +6° |

We claim:

1. A method of preparing a compound of the formula:

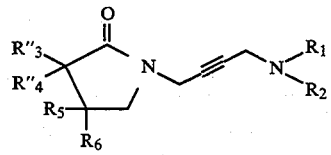

FORMULA I wherein $R_3''$ and $R_4''$ are selected from the group consisting of hydrogen, ($C_1$-$C_6$)alkyl or hydroxy; $R_5$ and $R_6$ are hydrogen; $R_1$ and $R_2$ are each ($C_1$-$C_6$)alkyl or $R_1$ is ($C_1$-$C_6$)alkyl and $R_2$ is —($CH_2$)$_n$—$R_{17}$, where n=2-6 and $R_{17}$ is selected from the group consisting of hydroxy, trialkylsilyloxy or $R_1$ and $R_2$ taken together with their associated N(itrogen) are selected from the group consisting of pyrrolidine, piperidine or moieties of the formula:

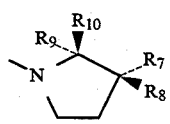

wherein $R_7$ and $R_8$ are independently selected from ($C_1$-$C_6$)alkoxy, trialkylsilyloxy or hydrogen; $R_9$ and $R_{10}$ are independently selected from hydrogen, hydroxymethyl or trialkylsilyloxymethyl with the proviso that only one of $R_7$, $R_8$, $R_9$ and $R_{10}$ can be one of the above disclosed substituents other than hydrogen; which comprises successively reacting a compound of general formula:

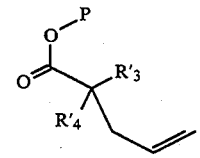

wherein P is ($C_1$-$C_6$)lower alkyl, arylmethyl or substituted cyclohexyl or substituted oxazalone; with ozone followed by zinc in acetic acid or a phosphine such as triphenylphosphine or a thioether such dimethylsulfide; then reacting the above product with a compound of formula:

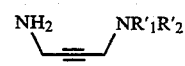

wherein $R'_1$ and $R'_2$ are each ($C_1$-$C_6$)alkyl or $R'_1$ is ($C_1$-$C_6$)alkyl and $R'_2$ is —($CH_2$)$_n$—$R_{17}$, where n=2-6 and $R_{17}$ is selected from the group consisting of hydroxy, trialkylsilyloxy or $R'_1$ and $R'_2$ taken together with their associated N(itrogen) are selected from the group consisting of pyrrolidine, piperidine or moieties of the formula:

wherein $R_7$ and $R_8$ are independently selected from the group consisting of ($C_1$-$C_6$)alkoxy, trialkylsilyloxy or hydrogen; and $R_9$ and $R_{10}$ are independently selected from hydrogen, hydroxymethyl, or trialkylsilyloxymethyl with the proviso that only one of $R_7$, $R_8$, $R_9$ and $R_{10}$ can be one of the above disclosed substituents other than hydrogen; and adding to the reaction mixture sodium cyanoborohydride and concomitant cyclization of the reduced intermediate.

* * * * *